US008945887B2

(12) United States Patent
Jose et al.

(10) Patent No.: US 8,945,887 B2
(45) Date of Patent: Feb. 3, 2015

(54) WHOLE CELL BIOCATALYST

(75) Inventors: Joachim Jose, Düsseldorf (DE); Ruth Maas, Düsseldorf (DE); Christian Detzel, Duisburg (DE)

(73) Assignee: Zyrus Beteiligungsgesellschaft mbH & Co. Patente I KG (DE)

( * ) Notice: Subject to any disclaimer, the term of this patent is extended or adjusted under 35 U.S.C. 154(b) by 436 days.

(21) Appl. No.: 13/509,935

(22) PCT Filed: Nov. 16, 2010

(86) PCT No.: PCT/EP2010/006951
§ 371 (c)(1),
(2), (4) Date: Sep. 13, 2012

(87) PCT Pub. No.: WO2011/057820
PCT Pub. Date: May 19, 2011

(65) Prior Publication Data
US 2013/0011890 A1    Jan. 10, 2013

(30) Foreign Application Priority Data

Nov. 16, 2009    (EP) .................................... 09014294

(51) Int. Cl.
*C12N 15/70* (2006.01)
*C12P 7/42* (2006.01)
*C12N 9/78* (2006.01)

(52) U.S. Cl.
CPC ... *C12P 7/42* (2013.01); *C12N 9/78* (2013.01); *C12N 15/70* (2013.01); *C07K 2319/034* (2013.01); *C07K 2319/035* (2013.01)
USPC ....... 435/136; 435/252.33; 435/471; 435/188

(58) Field of Classification Search
CPC combination set(s) only.
See application file for complete search history.

(56) References Cited

U.S. PATENT DOCUMENTS

| 6,180,359 B1 | 1/2001 | Favre-Bulle et al. ............ 435/43 |
| 6,869,783 B1 | 3/2005 | Ress-Loschke et al. ....... 435/135 |
| 2007/0178575 A1 | 8/2007 | Zhu et al. ...................... 435/228 |

FOREIGN PATENT DOCUMENTS

| CN | 101186933 | 5/2008 |
| RU | 98113063 A | 5/2000 |

OTHER PUBLICATIONS

Chinese Office Action, dated Apr. 15, 2013, from related Chinese Application No. 201080061731.7.
Zhang Jin-wen et al., "Cloning of bromoxynil-specific nitrilase gene (*bxn*) from *Klebsiella ozaenae* and expression in prokaryotic cells," Dec. 31, 2006, *Acta prataculturae Sinica*, vol. 15, No. 6, pp. 87-92 (English abstract on p. 92).

Banerjee, A., et al., (2002) "The nitrile-degrading enzymes: current status and future prospects", *Appl. Microbiol. Biotechnol.* 60:33-44.
Banerjee, A., et al,, (2008) "Enantioselective Nitrilase from *Pseudomonas putida*: Cloning, Heterologous Expression, and Bioreactor Studies", *Mol Biotechnol* [Epub ahead of print] 41(1):35-41 (published in Journal Jan. 2009).
Birnboim, H. C., et al., (1979) "A rapid alkaline extraction procedure for screening recombinant plasmid DNA", *Nucleic Acids Res.* 7(6):1513-1523.
Buchholz, Kasche und Bornscheuer (2005) "Biocatalysts and Enzyme Technology. Enzymes in Organic Chemistry," pp. 146-150, Wiley-VCH-Verlag, Weinheim.
Chen, R. R., (Mar. 2007) "Permeability issues in whole-cell bioprocesses and cellular membrane engineering", *Applied Microbiology and Biotechnology* 74(4):730-738.
Detzel, C., et al., (Feb. 2011) "Autodisplay of Nitrilase from *Alcaligenes faecalis* in *E coli* Yields a Whole Cell Biocatalyst for the Synthesis of Enantiomerically Pure (R)-Mandelic Acid", *Chemcatchem* 3:719-725.
Hartl, F. U., et al., (2002) "Molecular chaperones in the cytosol: from nascent chain to folded protein", *Science* 295:1852-1858.
Hantke K., (1981) "Regulation of ferric iron transport in *Escherichia coli* K12: isolation of a constitutive mutant", *Mol Gen Genet* 182:288-292.
Henderson, I. et al., 2004, "Type V protein secretion pathway: the autotransporter story", *Microbiology and Molecular Biology Reviews*, 68(4):692-744.
Jose, J., et al., (2001) "Funcional display of active bovine adrenodoxin on the surface of *E. coli* by chemical incorporation of the [2Fe—2S] cluster", *ChemBioChem* 2:695-701.
Jose, J., et al., (2002) "Cellular surface display of dimeric Adx and whole cell P450-mediated steroid synthesis on *E. coli*", *J. Biotechnol.*, 95:257-268.
Jose, J., et al., (2004) "Autodisplay of active sorbitol dehydrogenase (SDH) yields a whole cell biocatalyst for the synthesis of rare sugars", *ChemBioChem*, 5:491-499.
Jose, J., (2006) "Autodisplay: efficient bacterial surface display of recombinant proteins", *Appl. Microbiol. Biotechnol.* 69:607-614.
Jose, J., et al., (Dec. 2007) "The autodisplay story, from discovery to biotechnical and biomedical applications", *Microbiol Mol Biol Rev* 71(4):600-619.
Kaul, P., et al., (2007) "Cross-Linked Amorphous Nitrilase Aggregates for Enantioselective Nitrile Hydrolysis", *Adv Synth Catal* 349: 2167-2176.

(Continued)

*Primary Examiner* — Kagnew H Gebreyesus
(74) *Attorney, Agent, or Firm* — Greenberg Traurig, LLP

(57) ABSTRACT

The present invention relates to a method for producing a product of a reaction catalysed by a nitrilase, which method comprises the steps (i) providing a microorganism comprising said nitrilase located on its surface, and/or a membrane preparation of said microorganism, and (ii) contacting the microorganism and/or the membrane preparation thereof with one or more nitrilase substrates under conditions compatible with nitrilase activity. The present invention further relates to a method for producing enantiomerically pure (R)-mandelic acid using the nitrilase-displaying whole cell biocatalyst or membrane preparation thereof for the conversion of racemic mandelonitrile.

13 Claims, 18 Drawing Sheets

(56) References Cited

OTHER PUBLICATIONS

Figure 1:
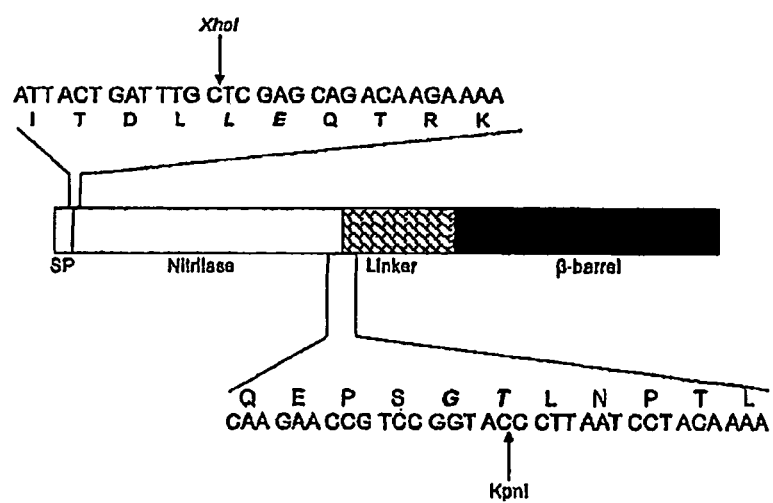

Kiziak, C., et al., (2005) "Nitrilase from *Pseudomonas fluorescens* EBC191: cloning and heterologous expression of the gene and biochemical characterization of the recombinant enzyme", *Microbiology* 151 (Pt 11): 3639-3648.

Luo, H., et al., (2008) "Gene Cloning, Overexpression, and Characterization of the Nilrilase from *Rhodococcus rhodochrous* tg1-A6 in *E. coli*." *Appl Biochem Biotechnol* 160:393-400 [published in Journal 2010] [Epub ahead of print].

Maurer, J., et al., (Feb. 1997) "Autodisplay: one-component sytem for efficient surface display and release of soluble recombinant proteins from *Escherichia coli*", *J. Bacteriol.* 1997, 179(3):794-804.

Nagasawa, T., et al., (1990) "A novel nitrilase, arylacetonitrilase, of *Alcaligenes faecalis* JM3, Purification and characterization", *Eur J Biochem* 194(3): 765-772.

Niewerth, U., et al., (Jan. 2001) "The AIDA Autotransporter System is Associated with F18 and Stx2e in *Escherichia coli* Isolates from Pigs Diagnosed with Edema Disease and Postweaning Diarrhea", *Clin. Diagn. Lab. Immunol.* 8(1):143-149.

Rey P., et al., (2004) "Hydrolysis of nitriles using an immobilized nitrilase: applications to the synthesis of methionine hydroxy analogue derivatives", *J Agric Food Chem* 52(26):8155-8162.

Rustler, S. et al., (2008) "Simultaneous expression of an arylacetonitrilase from *Pseudomonas fluorescens* and a (S)-oxynitrilase from *Manihot esculenta* in *Pichia pastoris* for the synthesis of (S)-mandelic acid", *Appl Microbiol Biotechnol* 80(1):87-97.

Singh, R., et al., (2005) "Release of an enantioselective nitrilase from *Alcaligenes faecalis* MTCC 126: a comparative study", *Bioprocess and Biosystems Engineering* 27:415-424.

Thimann, S., et al., (1964) "Nitrilase: I. Occurrence, preparation, and general properties of the enzyme", *Arch. Biochem. Biophys.* 105:133-141.

Thuku, R. N., et al., (2009) "Microbial nitrilases: versatile, spiral forming, industrial enzymes", *J. Appl. Microbiol.* 106:703-727.

Yamamoto, K. et al., (Oct. 1991) "Production of R-(−)-mandelic acid from mandelonitrile by *Alcaligenes faecalis* ATCC 8750", *Appl Environ Microbiol.* 57(10): 3028-3032.

Yamamoto, K., et al., (1992) "Purification and characterization of the nitrilase from *Alcaligenes faecalis* ATCC 8750 responsible for enantioselective hydrolysis of mandelonitrile", *J. Ferment. Bioeng.* 73:425-430.

International Search Report and Written Opinion, dated May 23, 2011, from corresponding International Application No. PCT/EP2010/006951.

WHOLE CELL BIOCATALYST

CROSS-REFERENCE TO RELATED APPLICATION

This patent application is a §371 national stage patent application based on International Patent Application No. PCT/EP2010/006951, filed Nov. 16, 2010, entitled "WHOLE CELL BIOCATALYST", which claims priority to European Patent Application No. 09014294.4, filed on Nov. 16, 2009, each of which is incorporated herein by reference in its entirety.

DESCRIPTION

The present invention relates to a method for producing a product of a reaction catalysed by a nitrilase, which method comprises the steps (i) providing a microorganism comprising said nitrilase located on its surface, and/or a membrane preparation of said microorganism, and (ii) contacting the microorganism and/or the membrane preparation thereof with one or more nitrilase substrates under conditions compatible with nitrilase activity. In particular, the present invention relates to a method for producing a carboxylic acid comprising the steps (i) providing a microorganism comprising a nitrilase on its surface, and/or a membrane preparation thereof, (ii) contacting the microorganism and/or the membrane preparation thereof with a nitrile such that the nitrilase may catalyse the conversion of nitrile to a carboxylic acid. The present invention further relates to a method for producing enantiomerically pure (R)-mandelic acid, using the nitrilase-displaying whole cell biocatalyst or membrane preparation thereof for the processing of racemic mandelonitrile.

Nitriles are important precursor molecules for producing a variety of products, e.g. carboxylic acids or amides (Banerjee et al., 2002). Due to the high stability of nitriles, however, it is necessary to subject them to strongly basic or acidic conditions at high temperatures for chemical conversion of nitriles (Banerjee et al., 2002; Nagasawa et al., 1990). Moreover, the purification of these products from the respective reaction mixture is very tedious.

Nitrilases (e.g. EC 3.5.5.1) are enzymes that are able to convert nitriles to the corresponding carboxylic acid and ammonia in a single step (Thimann and Mahadevan, 1964). The use of nitrilase enzymes has attracted substantial industrial interest, because, on the one hand, the carboxylic products are often used as intermediates in a great variety of chemical production processes and, on the other hand, nitrilases may be used for waste detoxification (Banerjee et al., 2002; Thuku et al., 2009). Furthermore, nitrilases are highly selective and yield enantiomerically pure carboxylic acids under mild conditions, without the need of cost intensive blocking and deblocking steps and catalysts necessary in conventional chemistry (Banerjee et al., 2002). Said high degree of selectivity renders possible a product synthesis which may not or only with difficulties be achieved using conventional methods.

The most important industrial application of nitrilases with regard to quantity is the conversion of racemic mandelonitrile to enantiomerically pure (R)-mandelic acid (Rey et al., 2004). (R)-mandelic acid used to separate enantiomers in a racemate using diastereomeric salts. Furthermore, it is an important chiral intermediate product in the chemical synthesis of new active agents.

It is well-known from literature that nitrilase from *A. faecalis* is able to convert mandelonitrile to mandelic acid with high enantioselectivity. Chiral carboxylic acids such as mandelic acid represent compounds desired in organic chemistry since they serve as basic products for a plurality of pharmaceutical agents or plant protection agents. Thus, for example, (R)- or (S)-mandelic acid are used for racemic resolution of racemic amines. Additionally, (R)-mandelic acid is used as an intermediate for the synthesis.

However, nitrilases have been characterised as notoriously unstable enzymes (Buchholz, Kasche and Bornscheuer, 2005) and are, consequently, rarely used as purified enzymes in industry or are used as whole cell preparation. The active center of nitrilases contains a catalytic sequence of three amino acid residues (catalytic triad) comprising a conserved active site cystein residue (Kobayashi et al., 1992) susceptible to autooxidation (Kobayashi et al., 1992) and reactive towards many chemicals such as thiol-containing reagents.

As long as present inside the cell, nitrilases are protected by the redox environment of the bacterial cytosol, which is reducing (Choi and Lee, 2004) and so prevents oxidation of thiol groups. However, nitrilases have been shown to lose activity upon exposure to oxygen, and this observation has been attributed to the susceptibility of the crucial redox-sensitive triad cystein in the active center (Mateo et al., 2006).

Several strategies have been employed to overcome the shortcomings of nitrilases in terms of insufficient activity and/or stability.

In one approach, whole nitrilase-expressing cells rather than purified enzyme preparations are used, which provide nitrilases intracellularly either in strain-specific or recombinant form (Kaul et al., 2007). For example, researchers have used *Alcaligenes faecalis* cells expressing nitrilase (Kaul, A. Banerjee and U. C. Banerjee, 2006) as whole cell catalysts comprising nitrilase located inside the cell. An enantiomeric excess of 97% has been achieved. The rationale underlying this approach is that the enzymes remain in their natural environment, the bacterial cytosol, where endogenous folding machineries and continuous turnover and protein biosynthesis maintain a constant level of stable and active protein. However, whole cell catalysts must be prepared and attached to a suitable matrix system (alginate) using time-consuming and labour-intensive procedures. Moreover, substrates to be turned over need to cross the selective bacterial cell membrane and face, once in the cytosol, a range of enzymes with alternative activities and competing substrates. Finally, whole cell catalysts contaminate preparations of desirable products and so rule out the use of such products for sensitive applications, for example the preparation of medical, cosmetic and hygienic products as well as beverages and foodstuffs.

Another approach towards the production of elevated levels of functional nitrilases for industrial use involved the use of chaperones. Chaperones of the GroEL family are essential proteins located in the cytosol that are required in order for cells to produce, through multiple rounds of ATP-dependent binding, encapsulation and release of substrate proteins, correctly folded proteins (Hartl, F. U. and Hayer-Hartl, M., 2002). Deletion of GroEL ultimately leads not only to lower levels of functional substrate proteins, but also to death of bacterial cells, owing to large quantities of unfolded accumulated protein. Chaperones, more specifically components of the GroEL system have been co-expressed with recombinant nitrilases in the cytosol of *E. coli* (U.S. Pat. No. 5,629,190, FIG. 9). This approach led to higher levels of soluble protein compared to cells with endogenous levels of chaperones only. However, the use of whole cells providing such folding machineries or the addition of separately purified chaperones and their cofactors and additional substrates to nitrilase preparations are prerequisites of such approaches.

U.S. Pat. No. 5,629,190 teaches the use of whole *E. coli* cells recombinantly expressing nitrilases. However, due to the particular intracellular enzyme equipment of the cells the resulting reactions are complex and their outcome unpredictable, even if a protein agent, such as GroEL, for assisting the folding of the polypeptides which the microorganism synthesizes, e.g. the recombinantly expressed nitrilase, is recombinantly expressed. As disclosed in U.S. Pat. No. 5,629,190, the nitrilase-catalysed conversion of the nitrile to the carboxylic acid competes with a nitrile hydratase-catalysed reaction (resulting in acid amide formation), leading to a yield reduction and undesired by-products which may be difficult to remove. Other enzymes present in the cell may modify the nitrile at the nitrite group or any other moiety.

Another approach involved the preparation and the use of cross-linked enzyme aggregates, i.e. the preparation of soluble recombinant enzyme and subsequent cross-linking using reactive bifunctional chemicals such as glutaraldehyde or poly(ethyleneimine). However, Kaul et al. (2007) have demonstrated that such immobilisation resulted in a significant reduction of reaction rates and a decreased specificity constant. In addition, chemical cross-linking led to altered substrate specificity, an observation that has been linked to the crosslinking process which may well have yielded protein molecules "locked" in a specific conformation. Moreover, batches of immobilised enzymes as well as their degradation products and debris may not be straightforward to separate from desirable reaction products.

Yamamoto et al. (1991) tested various isolates (wildtype strains) with respect to their ability to convert mandelonitrile into (R)-(−)-mandelic acid. *A. faecalis* strain ATCC 8750 was found to have the highest level of activity and enantioselectivity to produce (R)-(−)-mandelic acid from racemic mandelonitrile (Yamamoto et al., 1991). In particular, the (R)-(−)-mandelic acid made of mandelonitrile by resting cells was present in a 100% enantiomeric excess. *A. faecalis* ATCC 8750 has an (R)-enantioselective nitrilase and an amidase used to process mandelonitrile and mandelamide, respectively. As (R)-(−)-mandelic acid was produced from racemic mandelonitrile in a yield of 91%, whereas no (S)-mandelonitrile was left, the (S)-(−)-mandelonitrile remaining in the reaction is spontaneously racemised because of the chemical equilibrium of the (R)- and the (S)-isomer of mandelonitrile on the one hand and benzaldehyde/HCN on the other hand. Consequently, almost all the mandelonitrile is consumed and converted to (R)-(−)-mandelic acid. It is noted that, according to Yamamoto et al. (1991), the *A. faecalis* cells employed for production of (R)-mandelic acid require specifically optimized culture conditions.

Meanwhile different nitrilases of bacterial origin have been cloned and recombinantly expressed in *E. coli* (Kiziak et al., 2005; Luo et al., 2008; Rustler et al., 2008; U.S. Pat. No. 6,180,359; Ress-Löschke et al., 1998). The nitrilase has been biochemically characterized (Kiziak et al., 2005). It was also possible to recombinantly express the nitrilase gene of *A. faecalis* ATCC8750 in *E. coli*, which was then used in immobilisation experiments as "cross-linked enzyme aggregates" after purification (Rey et al., 2004). In this method the nitrilase has to be isolated from the host organism, i.e. *E. coli*, and purified. This approach is quite tedious. Moreover, the nitrilase may be deactivated in the course of the procedure.

The nitrilase from *Alcaligenes faecalis* subsp. *faecalis* ATCC 8750 has been described as a homooligomeric enzyme composed of approximately 14 subunits with a molecular weight of 32 kD per subunit, so the native protein has a total combined molecular weight of round about 460 kD (Yamamoto et al., 1992). In general, nitrilases exist as inactive dimers and form active oligomers through self-association. However, the number of subunits needed for activity differs from nitrilase to nitrilase (Thuku et al., 2009).

In summary, nitrilase has several shortcomings which hamper the use of nitrilase in production of organic compounds:

Nitrilases are sensitive against oxidation, resulting in a reduction of nitrilase activity over time When used in the form of a whole cell biocatalyst, undesired side reactions catalysed by other enzymes (such as nitrile hydratase) present in the cell may disturb the reaction catalysed by the nitrilase.

Nitrilase cannot be recovered from the reaction mixture.

Autodisplay represents an elegant tool for the bacterial surface display of recombinant proteins. This expression system is based on the secretion mechanism of the autotransporter family of proteins belonging to the type V secretion system.

In Gram-negative bacteria the autotransporter pathway evolved both for the transportation of proteins to the cell surface and the secretion of proteins into the extracellular milieu (Jose and Meyer, 2007). The autotransporter proteins are synthesized as precursor proteins containing all structural requirements for the transport to the cell surface (Jose, 2006). They are synthesized with an N-terminal signal peptide typical for the Sec pathway which enables the crossing of the inner membrane. Once in the periplasm, after truncation of the signal peptide, the C-terminal part of the precursor folds into the outer membrane as a porine-like structure, a so called β-barrel. Through this pore, the N-terminally attached passenger domain is translocated to the surface (Jose, 2002). There, it may be cleaved off—either autoproteolytically or by an additional protease—or remain anchored to the cell envelope through the transporter domain. Replacing the natural passenger by a recombinant protein results in its proper surface translocation. For this purpose an artificial precursor must be constructed by genetic engineering, consisting of a signal peptide, the recombinant passenger, the β-barrel and a linking region in between, which is needed to achieve full surface access. The AIDA-I autotransporter has been successfully used in this way for efficient surface display of various passenger domains (Henderson et al., 2004).

In the autodisplay system, self-association of subunits to an active enzyme has been observed, for instance in the dimeric enzyme sorbitol dehydrogenase (Jose, 2002; Jose and von Schwichow, 2004).

In particular, the autodisplay technology is an expression method for predetermined proteins on the surface of the outer membrane of *E. coli* and other Gram-negative bacteria, wherein the autodisplay system is based on the natural secretion mechanism of autotransporter proteins (Jose and Meyer, 2007). In this process, the recombinant passenger protein may be transported simply by introducing its coding sequence in-frame between the signal peptide and the translocating domain of the autodisplaying vector using standard methods of genetic engineering. The signal peptide may be obtained from the cholera toxin-subunit (CTB) and may be combined with an artificial promoter. Therefore, the passenger protein, intended for the translocation across the outer membrane, is expressed as a recombinant fusion protein with another protein called autotransporter at the outer membrane of *E. coli* (AIDA-I) (Jose, 2006). The C-terminal part of the auto-transporter proteins forms a porin-like structure (β-barrel) within the outer membrane of *E. coli*. This porin-like structure facilitates translocation of the recombinant passenger protein to the surface of the outer membrane of *E. coli* (Jose, 1995, 2006, 2007).

A problem underlying the present invention is to provide a method that allows for the production and preparation of nitrilases in an active state that is easily accessible to substrate molecules. Furthermore, the presence of other enzymes should be avoided in order to prevent undesired side reactions. A further problem underlying the present invention is to provide a method for producing products of reactions catalysed by a nitrilase (e.g. carboxylic acids) using recombinant nitrilases, wherein the problem of activity reduction over time is at least partially solved. Another problem underlying the present invention is to provide a method, wherein the product of a reaction catalysed by a nitrilase (e.g. carboxylic acid) may be easily recovered.

Surprisingly, the present inventors have found that a nitrilase may be expressed on the surface of a host cell, such as a microorganism, wherein the nitrilase is fully functional, i.e. capable of catalysing the conversion of nitriles resulting in the formation of a carboxylic acid.

A first aspect of the present invention is a method for producing a product of a reaction catalysed by a nitrilase, comprising the steps
(i) providing a microorganism comprising said nitrilase located on its surface, and/or a membrane preparation of said microorganism,
(ii) contacting the microorganism and/or the membrane preparation thereof with one or more nitrilase substrates under conditions compatible with nitrilase activity.

In the method of the present invention, any known substrate of nitrilases may be employed. The product may be any compound which is the product of a reaction catalysed by a nitrilase. "Conditions compatible with nitrilase activity" as employed herein include conditions wherein the nitrilase is active, i.e. wherein the nitrilase is capable of converting the one or more substrates into the products. Any known condition wherein the nitrilase is active may be used.

It is preferred that one or at least one nitrilase substrate employed in the method of the present invention is a nitrile. It is also preferred that the product obtained by the method of the present invention is a carboxylic acid. "Conditions compatible with nitrilase activity" may be conditions wherein the nitrilase catalyses the conversion of a nitrile resulting in formation of a carboxylic acid. A preferred embodiment of the present invention is a method for producing a carboxylic acid, which method comprises the steps
(i) providing a microorganism comprising a nitrilase located on its surface, and/or a membrane preparation thereof,
(ii) contacting the microorganism and/or the membrane preparation thereof with a nitrile such that the nitrilase catalyses the conversion of the nitrile resulting in formation of a carboxylic acid.

Optionally, the method of the present invention further comprises the step (iii) recovering the microorganism employed in step (ii).

As used herein, a reference to "step (i)", "step (ii)", or "step (iii)" is a reference to the respective step of the method for producing a product of a reaction catalysed by a nitrilase, and of the preferred method for producing a carboxylic acid, as described herein.

The present invention is based on the surprising finding that bacterial nitrilases, when fused to a suitable autotransporter system in a recombinant manner, are translocated to the surface of the bacterial cell and integrated in an active folded conformation into the bacterial membrane such that they remain catalytically competent for several days and may be used to catalyse industrially relevant reactions. This is especially surprising since the outer membrane of bacterial cells is lacking a protein folding machinery appropriate for cytosolic proteins. Furthermore, the present inventors found out that, most surprisingly, the enzyme is not deactivated following or during transfer of the redox-sensitive enzyme from the reducing bacterial cytosol to the outer membrane, where oxygen is present at elevated levels, creating a highly oxidative environment.

Without wishing to be bound by any theory, the present inventors assume that nitrilases, when immobilised on the surface of the bacterial cells by way of autodisplay, form aggregates or three dimensional structures that protect reactive catalytic amino acid residues from deactivation, even when exposed to the elevated oxygen levels and strong mechanical forces associated with vigorous shaking as part of routine methods used to grow large quantities of bacterial cells.

The whole cell biocatalyst described herein made it possible for the first time to provide an active nitrilase on the surface of a Gram-negative cell, such as $E.$ $coli$, which cell may be used for nitrile conversion and for the production of the corresponding carboxylic acid. In particular, the nitrilase-displaying whole cell biocatalyst described herein may be used for the biotechnological conversion of nitriles.

Importantly, said reaction is accomplished under mild conditions, with good production rates and without the generation of toxic by-products. In particular, the nitrilase expressed recombinantly on the surface of a microorganism is capable of catalysing the conversion of nitriles under mild conditions such as at a pH around 7.0.

As used herein, "whole cell biocatalyst" refers to a whole cell, in particular a microorganism, comprising a natural catalyst, such as a protein enzyme, in particular nitrilase, to perform chemical transformations on organic compounds, in particular on nitriles, wherein the natural catalyst is preferably located on the surface of the cell. According to the invention, the catalyst may be recombinantly expressed.

A bacterial cell comprises a range of compartments separated from each other by hydrophobic membranes. A Gram-positive bacterial cell comprises a plasma membrane which confines the cytosol, the inside of the cell. The plasma membrane is surrounded by a layer of peptidoglycans. By contrast, Gram-negative bacteria have, in addition to the plasma membrane, another membrane referred to as outer membrane. The term "surface", as used herein, preferably refers to the layer of the microorganism that is in contact with the environment, for example liquid culture medium. In a preferred embodiment of the present invention, the surface is the side of a Gram-negative bacterial cell that is in contact with the liquid culture medium. As used herein, the expressions "displayed on the surface" and "expressed on the surface" are used interchangeably and refer to localization of the nitrilase on the surface of a cell.

As used herein, "microorganism" refers to a host cell. The host cell according to the invention may be a prokaryotic or a eukaryotic microorganism, preferably a prokaryotic microorganism, more preferably a bacterial cell, even more preferably a Gram-negative bacterial cell. Most preferably the microorganism is an $E.$ $coli$ cell. The terms "microorganism" and "host cell" are used interchangeably herein.

As used herein "nitrilase" refers to a nitrilase enzyme, a catalytically active portion, derivative or analogue thereof, which catalyses the conversion of nitriles to carboxylic acids and ammonia. It should be noted that, as used herein, "derivative" or "analogue" of a molecule refers to a portion derived from or a modified version of the molecule. In the present invention, the nitrilase may be any nitrilase, such as a nitrilase capable of catalysing the conversion of a nitrile resulting in formation of a carboxylic acid. A preferred nitrilase is an enzyme according to EC 3.5.5.1 (also referred to as "nitrile aminohydrolase").

The nitrilase may display nitrilase activity only. The nitrilase may also be a multifunctional enzyme, which, in addition to other activities, displays nitrilase activity.

The skilled person knows a number of species providing nitrilases, which species include prokaryotes and eukaryotes. For instance, the nitrilase employed in the present invention may be obtained from *Bordetella, Klebsiella, Aspergillus, Alcaligenes, Saccharomyces, Burkholderia, Neurospora, Lachancea, Debaryomyces, Yarrowia, Candida, Kluyveromyces, Rhodococcus, Nocardia,* and/or *Rhizobium.* Examples of species providing a nitrilase which can be employed in the present invention are *Bordetella bronchiseptica, Klebsiella pneumoniae, Aspergillus niger, Alcaligenes faecalis, Saccharomyces cerevisiae, Burkholderia multivorans, Aspergillus fumigatus, Neurospora crassa, Lachancea thermotolerans, Debaryomyces hansenii, Yarrowia lipolytica, Candida glabrata, Kluyveromyces lactis, Rhodococcus rhodochrous, Nocardia* sp., *Rhizobium leguminosarum,* and/or *Nocardia farcinica.*

The nitrilase of the present invention is preferably obtained from *Alcaligenes, Klebsiella* and/or *Saccharomyces.* A more preferred nitrilase is selected from nitrilases obtained from *Alcaligenes faecalis, Klebsiella pneumoniae* and *Saccharomyces cerevisiae. Alcaligenes faecalis* may be *Alcaligenes faecalis* subsp. *faecalis. Klebsiella pneumoniae* may be *Klebsiella pneumoniae* subsp. *ozaenae.* An even more preferred nitrilase is an *Alcaligenes faecalis* nitrilase.

The nitrilase of the present invention may be selected from the group comprising the nitrilases P_887662 [GI:33600102, 1 May 2009, *Bordetella bronchiseptica* RB50], AAA25057 [GI:149175, 26 Apr. 1993, *Klebsiella pneumoniae*], NP_943299 [GI:38639530, 30 Apr. 2009, *Klebsiella pneumoniae*], P10045 [GI:115192, 20 Apr. 2009, *Klebsiella pneumoniae* subsp. *ozaenae*], XP_001389617 [GI:145230706, 28 Feb. 2008, *Aspergillus niger*], ACS13754 [GI:239738518, 15 Jun. 2009, *Alcaligenes* sp. ECU0401], BAA02684 [GI:216203, 16 Feb. 2008, *Alcaligenes faecalis*], CAK46957 [GI:134083480, 24 Mar. 2007, *Aspergillus niger*], EDV09642 [GI:190406375, 16 Jun. 2008, *Saccharomyces cerevisiae* RM11-1a], YP_001945058 [GI:189349430, 7 May 2009, *Burkholderia* multivorans ATCC 17616], NP_012102 [GI:6322027, 16 Jun. 2008, *Saccharomyces cerevisiae* RM11-1a], 1F89B [GI:16975400, 19 Nov. 2001, *Saccharomyces cerevisiae*], NP_012409 [GI:6322335, 5 Nov. 2009, *Saccharomyces cerevisiae*], EDN63257 [GI:151945002, 13 Jul. 2007, *Saccharomyces cerevisiae* YJM789], EDN59257 [GI:151940875, 13 Jul. 2007, *Saccharomyces cerevisiae* YJM789], CAY80342 [GI:259147089, 23 Sep. 2009, *Saccharomyces cerevisiae* EC1118], EEU05439 [GI:256270219, 20 Aug. 2009, *Saccharomyces cerevisiae* JAY291] P40447 [GI:731891, 3 Nov. 2009, *Saccharomyces cerevisiae*], XP_751200 [GI:70992703, 27 Feb. 2008, *Aspergillus fumigatus* Af293], CAD71250 [GI:28950282, 14 Nov. 2006, *Neurospora crassa*], CAK48039 [GI:134075478, 24 Mar. 2007, *Aspergillus niger*], CAR23067 [GI:238934886, 8 Oct. 2009, *Lachancea thermotolerans*], CAG86637 [GI:199431326, 10 Sep. 2008, *Debatyomyces hansenii*], XP_500602 [GI:50546150, 29 Oct. 2008, *Yarrowia lipolytica*], CAG78819 [GI:49651877, 23 Oct. 2008, *Yarrowia lipolytica*], CAG59341 [GI:49525722, 16 Dec. 2008, *Candida glabrata*], XP 454637 [GI:50309261, 18 Apr. 2008, *Kluyveromyces lactis*], P20960 [GI:417386, 5 May 2009, *Alcaligenes faecalis*] ABO46008 [GI:134034945, 5 Nov. 2009, *Rhodococcus rhodochrous*], AAX18182 [GI:60280369, 2 Mar. 2005, *Nocardia* sp. C-14-1], BAA02127 [GI:216932, 16 Feb. 2008, *Rhodococcus rhodochrous*], Q02068 [GI:417382, 20 Jan. 2009, *Rhodococcus rhodochrous*], CAK02877 [GI:115259785, 13 May 2009, *Rhizobium leguminosarum* bv. *viciae* 3841], CAF05970 [GI:40882143, 10 Oct. 2009, *Neurospora crassa*], CAK08726 [GI:115257629, 13 May 2009, *Rhizobium leguminosarum* bv. *viciae* 3841], BAD58116 [GI:54016746, 10 May 2008, *Nocardia farcinica* IFM 10152], and Q5Z1U0 [GI:81603033, 3 Nov. 2009, *Nocardia farcinica*]. This list employed the format "Genbank accession number [Genbank Identifier, Date of database entry, species/strain]". The sequences of the nitrilases of this group can be identified by the Genbank accession number, the Genbank Identifier (GI), the date of the Genbank database entry, and the species and/or the strain from which the sequence is obtained.

The term "nitrilase", as employed herein, includes any nitrilase having an identity of at least 70%, at least 80%, at least 90%, at least 95%, at least 98%, or at least 99% with a nitrilase disclosed herein. The skilled person knows suitable methods for determination of the degree of identity on the level of the amino acid sequence, for instance by BLAST or PBLAST.

As indicated above, an active nitrilase may be a homooligomeric enzyme composed of approximately 14 subunits. In general, nitrilases exist as inactive dimers. In the present invention, the nitrilase displayed on the surface of the host cell may be a homomultimer comprising three or more identical subunits. In particular, the homomultimer may comprise from 7 to 16 identical subunits, such as 7, 8, 9, 10, 11, 12, 13, 14, 15, or 16 identical subunits. A number of approximately 14 subunits, i.e. 11, 12, 13, 14, 15, or subunits, is preferred. Homomultimers (also termed herein as "Homooligomers") may be formed by a spontaneous association of several identical polypeptide subunits displayed on the host cell membrane.

As used herein, "nitrile" refers to any compound comprising at least one —CN functional group (nitrile group). The nitrile may also comprise one, two, three, four or even more nitrile groups.

The nitrile group may be coupled to an aromatic moiety, such as an aryl group containing from 6 to 14 carbon atoms, preferably from 6 to 10 carbon atoms. The aryl group may comprise one, two, or three condensed aromatic rings. More preferably, the aryl group may be a phenyl group. The aryl group may be substituted by one or more substituents, such as one, two, three, four, five or even more substituents.

The nitrile group may be coupled to an aliphatic moiety, such as an alkyl group comprising 1 to 8 carbon atoms, 1 to 6 carbon atoms, 1 to 4 carbon atoms, or 1 to 3 carbon atoms. The alkyl group may be straight chain or branched. The alkyl group may comprise a cyclic moiety. The alkyl group may be substituted by one or more substituents, such as one, two, three, four, five or even more substituents.

The nitrile may comprise an alkyl aryl group, wherein alkyl and aryl have the meanings as described herein. The at least one nitrile group may be coupled to the alkyl group and/or the aryl group. The alkyl and/or aryl moiety may be substituted by one or more substituents, such as one, two, three, four, five or even more substituents.

The one or more substituents employed herein may be independently selected from —OH, iodo, bromo, chloro, fluoro, aryl, alkyl, alkoxy, and the like, wherein alkyl and aryl have the meanings as described herein, and alkoxy comprises 1 to 8 carbon atoms, 1 to 6 carbon atoms, 1 to 4 carbon atoms, or 1 to 3 carbon atoms. A preferred alkoxy group is methoxy.

The alkoxy group may be straight chain or branched. The alkoxy group may comprise a cyclic moiety.

The alkyl group, the aromatic group, and/or the alkoxy group may independently comprise at least one heteroatom, such as one, two, three, four, or even more heteroatoms, such that the at least one heteroatom replaces a carbon atom. The heteroatoms may independently be selected from N, O, and S.

Exemplary nitriles for use as a substrate of the nitrilase of the invention are aromatic nitriles such as mandelonitrile, benzonitrile, phenylpropionitrile, phenylgycinonitrile, bromoxynile, ioxynile, chloroxynile, anisonitrile, 3-bromo-4-hydroxybenzonitrile, 3-fluoro-4-hydroxybenzonitrile, 4-hydroxy-3,5-dimethobenzonitrile and prunasin; and aliphatic nitriles such as n-butyronitrile, n-valeronitrile, iso-butyronitrile and succinonitrile. A particularly preferred substrate of the invention is mandelonitrile.

According to the present invention, preferred substrates for the nitrilase from *Alcaligenes faecalis* are mandelonitrile and prunasin. Preferred substrates for the nitrilase from *Klebsiella pneumoniae* are bromoxynile, ioxynile, chloroxynile, anisonitrile, 3-bromo-4-hydroxybenzonitrile, 3-fluoro-4-hydroxybenzonitrile and 4-hydroxy-3,5-dimethobenzonitrile. Preferred substrates for the nitrilase from the *Saccharomyces cerevisiae* are benzonitrile, phenylprobionitrile, mandelonitrile, phenylglycinonitrile, n-butyronitrile, n-valeronitrile, isobutyronitrile and succinonitrile.

In one aspect of the invention, the gene encoding the nitrilase has been amplified from the whole DNA of *Alcaligenes faecalis* by means of PCR and cloned. The gene could be fused correctly with the reading frame of the autotransporter by means of suitable restriction sites attached to the PCR primer. The expression of the fusion protein could be shown with standard laboratory methods. The enzyme, which is expressed on the surface and immobilised thereon, is able to extracellularly convert an added substrate (in this case, racemic mandelonitrile).

With the culturing and expression conditions currently applied, a transformation rate of about 50%, preferably about 60%, more preferably about 70% and even more preferably about 80% after 5 days may be achieved. Compounds having an asymmetric C atom may be produced by the method of the present invention in an enantiomeric excess. The enantiomeric excess (% ee) may be at least about 50%, 60%, 70%, 80%, 90%, 95%, 96%, 97%, 98% or 99%, preferably at least about 99% or higher for the product, in particular for carboxylic acid. In particular for (R)-mandelic acid a transformation rate of about 80% after 5 days and an enantiomeric excess (% ee) of higher than 99% was achieved, as was shown by chiral HPLC.

As used herein, the enantiomeric excess (ee) of a substance is a measure of the optical purity of a substance. The enantiomeric excess may be determined in a solution of the compound to be analysed. Appropriate solvents (such as hydrophobic and hydrophilic solvents) and mixture's thereof are known.

The enantiomeric excess can be calculated by the following equation:

$$ee\% = 100 * ([R]-[S])/([R]+[S])$$

wherein [R], [S] indicates the concentration of the species; and wherein R and S refer to the (R)- and (S)-isomers, respectively. Thus, in a racemic mixture, i.e. [R]=[S], ee %=100*0/([R]+[S])=0%, i.e. there is no excess of R over S or vice versa. Therefore, the enantiomeric excess of a racemic mixture is 0%, whereas the enantiomeric excess of an enantiomerically pure compound is 100%. The concentration of the (R)- and (S)-isomer may be determined by any method known in the art for the determination of compounds having asymmetric C-atoms, such as but not limited to, determination of the specific rotation of the mixture, chiral column chromatography (e.g. chiral HPLC) and NMR spectroscopy.

The invention described herein has the advantage that the mild reaction conditions during the hydrolysis of nitrile are combined with an easy method of purifying the product, since the cells only have to be centrifuged from the reaction batch for this purpose.

The nitrilase may be recombinantly expressed in a microorganism and transported to the cell surface. A microorganism propagates independently and produces the enzyme itself so that the elaborate purification of the biocatalyst is no longer necessary. An example for such a microorganism is the *E. coli* strain described in Example 1 herein.

The term "recombinant", as used herein, refers to a nucleic acid sequence made of at least two nucleic acid sequences operatively linked to each other that are not naturally linked to each other. The at least two sequences may be obtained from the same organism. For example, a recombinant construct may comprise the signal sequence of an *Alcaligenes* species and the coding nitrilase sequence of the same *Alcaligenes* species, which is not normally linked to said signal sequence. The at least two sequences may be obtained from at least two different organisms. For instance, a signal peptide of *E. coli*, a nitrilase gene from *Alcaligenes*, a transmembrane linker from *E. coli*, and an autotransporter domain from *E. coli* may be operatively linked. Another example is a recombinant polypeptide wherein the signal peptide is derived from the cholera toxin β subunit (CTB), the autotransporter domain and the transmembrane linker are originated from *E. coli*, and the nitrilase is derived from *Alcaligenes*.

In a preferred embodiment of the present invention, the term "expressing recombinantly", also used synonymously with the term "expressed in a recombinant manner" or the like, as used herein, refer to the expression of a recombinant nucleic acid sequence. For example, the expression in *E. coli*, or indeed any organism, of a nucleic acid sequence comprising an *E. coli* signal peptide and an *Alcaligenes* nitrilase sequence constitutes a recombinant expression.

It is preferred that the nitrilase is fused to a transporter domain of an autotransporter. The transporter domain of the autotransporter according to the invention can be any transporter domain of an autotransporter and is preferably capable of forming a β-barrel structure. A detailed description of the β-barrel structure and preferred examples of β-barrel autotransporters are disclosed in WO97/35022 incorporated herein by reference. Henderson et al. (2004) describe autotransporter proteins which comprise suitable autotransporter domains (for summary, see Table 1 of Henderson et al., 2004). The disclosure of Henderson et al., (2004) is included herein by reference. For example, the transporter domain of the autotransporter may be selected from Ssp (P09489, *S. marcescens*), Ssp-h1 (BAA33455, *S. marcescens*), Ssp-h2 (BAA11383, *S. marcescens*), PspA (BAA36466, *P. fluorescens*), PspB (BAA36467, *P. fluorescens*), Ssa1 (AAA80490, *P. haemolytica*), SphB1 (CAC44081, *B. pertussis*), AspA/NalP (AAN71715, *N. meningitidis*), VacA (Q48247, *H. pylori*), AIDA-I(Q03155, *E. coli*), IcsA (AAA26547, *S. flexneri*), MisL (AAD16954, *S. enterica*), TibA (AAD41751, *E. coli*), Ag43 (P39180, *E. coli*), ShdA (AAD25110, *S. enterica*), AutA (CAB89117, *N. meningitidis*), Tsh (I54632, *E. coli*), SepA (CAC05786, *S. flexneri*), EspC (AAC44731, *E. coli*), EspP (CAA66144, *E. coli*), Pet (AAC26634, *E. coli*), Pic (AAD23953, *E. coli*), SigA (AAF67320, *S. flexneri*), Sat (AAG30168, *E. coli*), Vat (AAO21903, *E. coli*), EpeA (AAL18821, *E. coli*), EatA (AAO17297, *E. coli*), Espl (CAC39286, *E. coli*), EaaA (AAF63237, *E. coli*), EaaC (AAF63038, *E. coli*), Pertactin (P14283, *B. pertussis*), BrkA (AAA51646, *B. pertussis*), Tef (AAQ82668, *B. pertussis*), Vag8 (AAC31247, *B. pertussis*), PmpD (O84818, *C. trachomatis*), Pmp20 (Q9Z812, *C. pneumoniae*), Pmp21 (Q9Z6U5, *C. pneumoniae*), IgA1 protease (NP_283693, *N. meningitidis*), App (CAC14670, *N. meningitidis*), IgA1 protease (P45386, *H. influenzae*), Hap (P45387, *H. influenzae*), rOmpA (P15921, *R. rickettsii*), rOmpB (Q53047, *R. rickettsii*), ApeE (AAC38796, *S. enterica*), EstA (AAB61674, *P. aeruginosa*), Lip-1 (P40601, *X. luminescens*), McaP (AAP97134, *M. catarrhalis*), BabA (AAC38081, *H. pylori*), SabA (AAD06240, *H. pylori*), AlpA (CAB05386, *H. pylori*), Aae (AAP21063, *A. actinomycetemcomitans*), NanB (AAG35309, *P. haemolytica*), and variants of these autotransporters. Given in brackets for each of the exemplary autotransporter proteins are examples of suitable genbank accession numbers and species from which the autotransporter may be obtained. Preferably the transporter domain of the autotransporter is the *E. coli* AIDA-I protein or a variant thereof, such as e.g. described by Niewert U., Frey A., Voss T., Le Bouguen C., Baljer G., Franke S., Schmidt M A. The AIDA Autotransporter System is Associated with F18 and Stx2e in *Escherichia coli* Isolates from Pigs Diagnosed with Edema Disease and Postweaning Diarrhea. Clin. Diagn. Lab. Immunol. 2001 January, 8 (1):143-149; 9.

Variants of the above indicated autotransporter sequences may e.g. be obtained by altering the amino acid sequence in the loop structures of the β-barrel which are not part of the transmembrane portions. Optionally, the nucleic acid portions coding for the surface loops may be deleted completely. Moreover, conserved amino exchanges, i.e. the exchange of an hydrophilic to another hydrophilic amino acid and/or the exchange of a hydrophobic to another hydrophobic amino acid may take place within the amphipathic β-sheet. Preferably, a variant has a sequence identity of at least 70%, at least 80%, at least 90%, at least 95% or at least 98% on the amino acid level to the respective native sequence of the autotransporter domain, in particular in the range of the β-sheets.

It is preferred that step (i) of the method of the invention comprises the steps:
 (a) providing a microorganism comprising a nucleic acid sequence operatively linked with an expression control sequence, said nucleic acid sequence comprising:
  (1) a portion encoding a signal peptide,
  (2) a portion encoding a recombinant nitrilase to be displayed,
  (3) optionally a portion encoding a protease recognition site,
  (4) a portion encoding a transmembrane linker, and
  (5) a portion encoding the transporter domain of an autotransporter,
 (b) culturing the microorganism under conditions, wherein the nucleic acid sequence of (a) is expressed and the expression product of the nucleic acid sequence is displayed on the surface of the microorganism.

The person skilled in the art is able to devise conditions wherein the nucleic acid sequence is expressed, and this involves routine experimentation only, for example testing various temperatures, media, cell densities and/or concentrations of expression-inducing chemicals.

The microorganism provided according to step (a) may be obtained by transformation with a nucleic acid sequence operatively linked with an expression control sequence, wherein said nucleic acid comprises:
 (1) a portion encoding a signal peptide,
 (2) a portion encoding a recombinant nitrilase to be displayed,
 (3) optionally a portion encoding a protease recognition site,
 (4) a portion encoding a transmembrane linker, and
 (5) a portion encoding the transporter domain of an autotransporter,
wherein the components (1) to (5) are nucleic acid sequences as described hereinbelow.

Any known method of transformation can be used. The term "transformed", as used herein, preferably refers to the introduction of a heterologous construct into a cell, preferably a bacterial cell, which is henceforth referred to as being transformed. The person skilled in the art knows about transformation protocols and procedures, for example, electrotransformation or transformation of chemically competent cells.

In another embodiment, the inventive method further comprises the step
 (c) producing a membrane preparation from the microorganism of (b).

The membrane preparation employed in the present invention comprises a catalytically active nitrilase. The term "membrane preparation", as used herein, preferably refers to a product enriched in membrane components. The person skilled in the art is familiar with protocols and procedures that can be used to obtain membrane preparations. For example, bacterial cells may be harvested from a culture and subjected to lysis, e.g. by way of freeze-thaw cycles, sonication, resuspension in lysis buffers or the like, followed by differential centrifugation to isolate membrane fractions of the cells. In a preferred embodiment of the present invention, the membrane preparation is an outer membrane preparation, i.e. a preparation enriched in components of the outer membrane relative to components of other membranes and compartments such as the cytosol, the inner membrane and the periplasm. The person skilled in the art is familiar with protocols and procedures that can be used to isolate the outer membrane, for example lysozyme treatment of bacterial cells and subsequent centrifugation steps. In a preferred embodiment of the present invention, the membrane preparation is an outer membrane preparation comprising a catalytically active nitrilase, which membrane preparation is made of cells that synthesise said nitrilase in the cytosol and subsequently transport it to the outer membrane. In another embodiment, said membrane preparation may be adequately processed, for example by incorporating membrane proteins, such as a nitrilase fusion protein, into artificial vesicles. The person skilled in the art has ways of functionally reconstituting membrane proteins in vesicles, for example using suitable, detergents.

Step (a) of the method of the present invention refers to the provision of a microorganism. The microorganism may be any microorganism described herein. In step (a), a host cell, particularly a host bacterium is provided which comprises a nucleic acid sequence operatively linked with an expression control sequence, i.e. a promoter, and optionally further sequences required for gene expression in the respective host cell. As used herein, "a nucleic acid sequence operatively linked with an expression control sequence" refers to the functional relationship of a nucleic acid sequence with an expression control sequence. The skilled person knows suitable promoters and expression control sequences. The promoter and/or the expression control sequence may be homologous or heterologous to the host cell.

Preferably, the nucleic acid sequence is located on a recombinant vector, e.g. a plasmid vector.

The nucleic acid sequence according to step (a) comprises (1) a portion encoding a signal peptide, preferably a portion coding for a Gram-negative signal peptide allowing for transport into the periplasm through the inner cell membrane. The signal peptide may be a signal peptide homologous to the host cell. The signal peptide may also be a signal peptide heterologous to the host cell.

Further, the nucleic acid sequence comprises (2) a portion encoding the nitrilase to be displayed ("=passenger polypeptide" or "passenger"). A nucleic acid encoding any nitrilase as described herein may be employed.

The nucleic acid sequence optionally comprises (3) a portion encoding a protease recognition site. The term "protease recognition site", as used herein, refers to a specific amino acid sequence that is recognised by a specific protease which subsequently cleaves the polypeptide by way of hydrolysis of an amide bond marked by the protease recognition site. The protease recognition site may be a recognition site for an intrinsic protease, i.e. a protease naturally occurring in the host cell, or an externally added protease. For example, the externally added protease may be an IgA protease (cf. EP-A-0 254 090), thrombin or factor X. The intrinsic protease may be e.g. selected from OmpT, OmpK or protease X. The protease recognition site may be homologous to the host cell. The protease recognition site may also be heterologous to the host cell.

Furthermore, the nucleic acid sequence comprises (4) a portion encoding a transmembrane linker which is required for the presentation of the passenger polypeptide, i.e. a recombinant nitrilase (2) on the outer surface of the outer membrane of the host cell. A transmembrane linker domain may be used which is homologous with regard to the autotransporter, i.e. the transmembrane linker domain is encoded by a nucleic acid portion directly fused to the 5' end of the nucleic acid sequence encoding the autotransporter domain. Also a transmembrane linker domain may be used which is heterologous with regard to the autotransporter. The length of the transmembrane linker is preferably 30-160 amino acids.

Further, the nucleic acid sequence comprises (5) a portion encoding a transporter domain of an autotransporter. In the context of the present invention, autodisplay may be the recombinant surface display of proteins or polypeptides by means of an autotransporter in any Gram-negative bacterium. The transporter domain may be any transporter domain described herein.

The components (1) to (5) in the nucleic acid sequence of the present invention are preferably oriented from 5' to 3'. In the expression product obtained in step (b), the amino acid sequences encoded by nucleic acid sequences (1) to (5) are preferably arranged N terminal to C terminal.

Step (b) of the method of the present invention refers to culturing the microorganism under conditions wherein the nucleic acid sequence of step (a) is expressed and the expression product comprising the recombinant nitrilase is displayed on the surface of the microorganism. The person skilled in the art knows suitable culture conditions. The method according to the invention allows for an efficient expression of passenger proteins on the surface of microorganisms, particularly E. coli or other gram-negative bacterial cells up to 100 000 or more molecules per cell by using a liquid medium of the following composition: 5 g/l to 20 g/l, preferably about 10 g/l trypton, 2 g/l to 10 g/l, preferably about 5 g/l yeast extract, 5 g/l to 20 g/l, in particular about 10 g/l NaCl and the remaining part water. The medium should possibly contain the lowest possible amount of divalent cations, thus preferably Aqua bidest or highly purified water, e.g. Millipore water is used. The liquid medium may contain in addition preferably EDTA at a concentration of 2 $\mu$M to 20 $\mu$M, in particular 10 $\mu$M. Moreover, it may contain preferably reducing reagents, such as 2-mercapto ethanol or dithiotreitol or dithioerythritol in a preferred concentration of 2 mM to 20 mM. The reducing reagents favour a non-folded structure of the polypeptide during transport. The liquid medium may further contain additional C-sources, preferably glucose, e.g. in an amount of up to 10 g/l, in order to favour secretion, i.e. transfer of the passenger to the surrounding medium. For surface display preferably no additional C-source is added. Preferred culture conditions for Gram-negative cells, such as E. coli, are described in the Examples.

Step (ii) may be performed under aerobic and/or oxidising conditions. In a preferred embodiment, the term "aerobic conditions" refers to conditions characterised by the presence of oxygen. In another preferred embodiment, the term "aerobic conditions", refers to the presence of elevated levels of oxygen compared to levels normal with regard to the given temperature and liquid. In another preferred embodiment, the term "aerobic" conditions refers to conditions characterised by elevated gas exchange between a liquid, for instance a culture medium, and the surrounding gas environment comprising oxygen, for example air. The person skilled in the art is able to measure oxygen levels, for example through the use of suitable oxygen-sensitive electrodes. Moreover, the person skilled in the art is able to bring about aerobic conditions, for example by flushing buffers or media with air or oxygen, by adding oxygen-releasing chemicals or simply by vigorously shaking such buffers or media in the presence of oxygen or air. By contrast, the person skilled in the art is able to bring about anaerobic conditions, for example by flushing media or buffers extensively with argon or nitrogen, or by sealing culture vessels in order to minimise gas exchange.

In a preferred embodiment, the term "oxidising conditions", as used herein, refers to the addition to media or buffers or the presence of oxidants, i.e. chemicals that cause other chemicals to release electrons, in which enzymes tend to get oxidised. For example, reduced redox enzymes tend to oxidise in the presence of oxygen. By contrast, the term "reducing" or "reducing conditions", as used herein, refers to the addition to media or buffers or the presence of reductants, i.e. chemicals that cause other chemicals to take up electrons. The person skilled in the art is able to set up the redox environment of choice, for example through the addition of oxidants, such as oxygen, and the addition of reductans, for example thiol reagents such as mercaptoethanol or DTT. Moreover, the person skilled in the art is able to measure the redox potential of solutions, for example through the use of redox electrodes.

In a Gram-negative bacterial host cell, such as E. coli, after translocation of the recombinant passenger, the passenger remains attached to the surface of the outer membrane by the $\beta$-barrel, which serves as an anchor within the outer membrane. Due to the controlled integration of the $\beta$-barrel within the outer membrane, the C terminal part of the $\beta$-barrel is directed to the inner side of the outer membrane, whereas the N-terminal part of the linker, to which the recombinant passenger protein is covalently bound, is directed to the outer surface of the outer membrane, i.e. the environment.

The optional step (c) refers to the production of a membrane preparation from the microorganism of step (b). Suitable methods to obtain a membrane preparation are well-known to a person skilled in the art.

The membrane preparation as used herein is preferably an outer membrane preparation.

Step (ii) of the method of the present invention refers to contacting the microorganism and/or the membrane preparation thereof with one or more nitrilase substrates under conditions compatible with nitrilase activity. As indicated above, in a preferred embodiment, step (ii) refers to contacting the microorganism and/or the membrane preparation thereof with a nitrile under conditions wherein the nitrilase catalyses conversion of the nitrile resulting in formation of a carboxylic acid. Any suitable condition know in the art may be employed. In particular, the reaction is performed in a liquid medium. In a liquid medium, the microorganism may form a suspension. The microorganism may also be immobilized. If a membrane preparation is employed, the membrane preparation may form particles which may be dispersed in a liquid medium. The reaction may be performed at a pH in the range of about 5.0 to about 9.0, preferably about 6.0 to about 8.0 and more preferably about 6.5 to about 7.5.

Step (iii) of the method of the present invention refers to the recovery of the microorganism, which microorganism is employed in step (ii). As demonstrated by the examples of the present invention, after a reaction cycle of for instance 24 h, the bacterial cells still exhibit significant activity. Hence, the cell can be employed in a further reaction cycle. Recovery may be performed by centrifugation of the reaction mixture. If required, cells may be washed.

Another aspect of the invention relates to the use of a microorganism expressing a nitrilase on the surface and/or a membrane preparation thereof, for the production of a product of a reaction catalysed by a nitrilase, in particular for the production of a carboxylic acid. It is preferred that the carboxylic acid produced is mandelic acid, particularly (R)-mandelic acid.

Another aspect of the invention relates to a microorganism displaying a recombinant nitrilase on the surface, wherein the microorganism is a microorganism as described herein, and the nitrilase is a nitrilase as described herein. In particular, the microorganism displays a fusion polypeptide comprising a signal peptide, a recombinant nitrilase, an optional protease recognition site, a transmembrane linker, and a transporter domain of an autotransporter on its surface, wherein the components of the fusions proteins are as described herein.

Still another aspects of the invention relates to a membrane preparation comprising a nitrilase. The membrane preparation may be obtained from a microorganism as described herein, for instance in step (c) of the method of the present invention. The nitrilase may be any nitrilase as described herein.

Yet another aspect of the invention is a method for producing a microorganism displaying a recombinant nitrilase on its surface comprising introducing a nucleic acid sequence into said microorganism, said nucleic acid sequence comprising:
(1) a portion encoding a signal peptide,
(2) a portion encoding a recombinant nitrilase to be displayed,
(3) optionally a portion encoding a protease recognition site,
(4) a portion encoding a transmembrane linker, and
(5) a portion encoding the transporter domain of an autotransporter,
wherein the nucleic acid is operatively linked with an expression control sequence. The components (1) to (5) are nucleic acid sequences as described hereinabove. The microorganism may be any microorganism as described herein, such as a bacterium, more particular a Gram-negative bacterium, even more particular *E. coli*.

The nitrilase may be any nitrilase as described herein. "Introducing a nucleic acid into said microorganism" includes transformation, as described herein.

The invention is further illustrated by the following Figures and Examples which should not be considered as limiting the scope of the invention:

FIG. 1: Scheme of the autotransporter fusion protein encoded by pAT-NitAf. The environment of the fusion sites is given as sequences. The two amino acids at the N-terminus which were added due to the cloning procedure are shown in italics and bold. The signal peptidase cleavage site is indicated. SP, signal peptidase.

Figure 2:
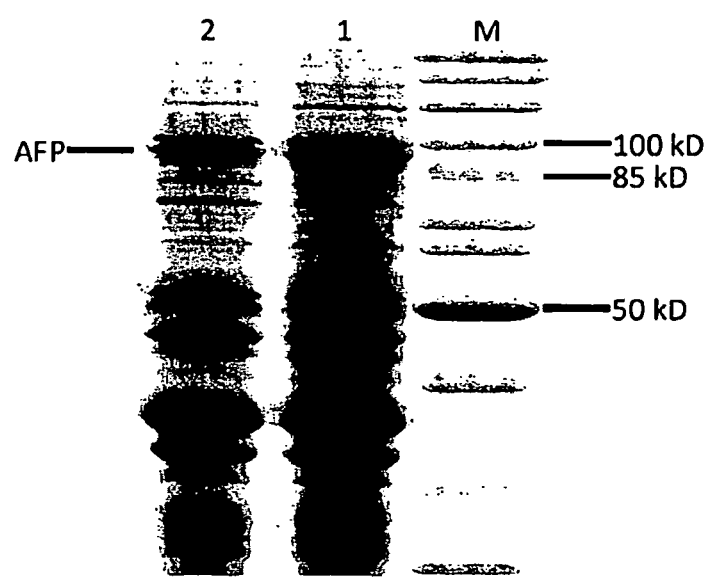

FIG. 2: SDS-PAGE of the outer membrane fraction of *E. coli* BL21 (DE3) pAT-NitAf comprising the overexpressed autotransporter fusionprotein AFP (1), whole cell digestion of the overexpressed autotransporter with proteinase K (2) and marker lane (M).

Figure 3:
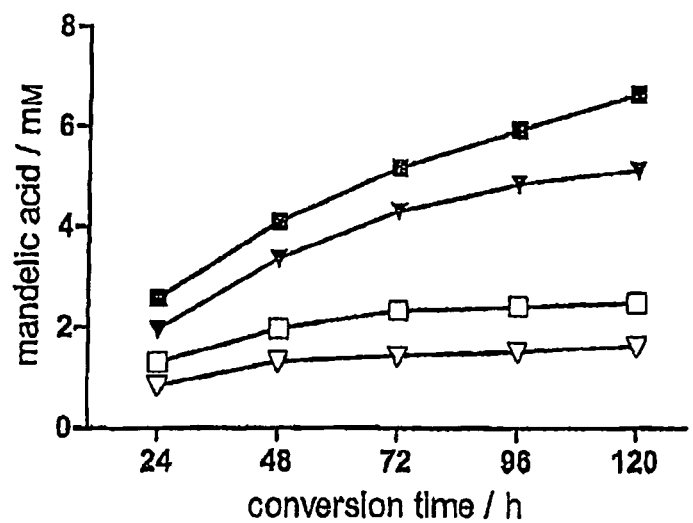

FIG. 3: Demonstration of the nitrilase activity:
Production of (R)-mandelic acid from (R,S)-mandelonitrile The reaction mixture contained, in a total volume of 1 ml, Na-phosphate buffer (50 mM, pH 7.5), (R,S)-mandelonitrile (10 mM) and cells of *E. coli* BL21 (DE3) pAT-NitAf corresponding to an $OD_{578}$ of 10. Data points are the average of triplicate experiments; the bars representing standard errors are too small to be visible. Filled symbols represent induction at $OD_{578}$ 1 and open symbols represent induction at $OD_{578}$ 0.5. Tris-HCl buffer pH 7 (▼/▽), phosphate buffer pH 7.5 (■/□).

Figure 4:
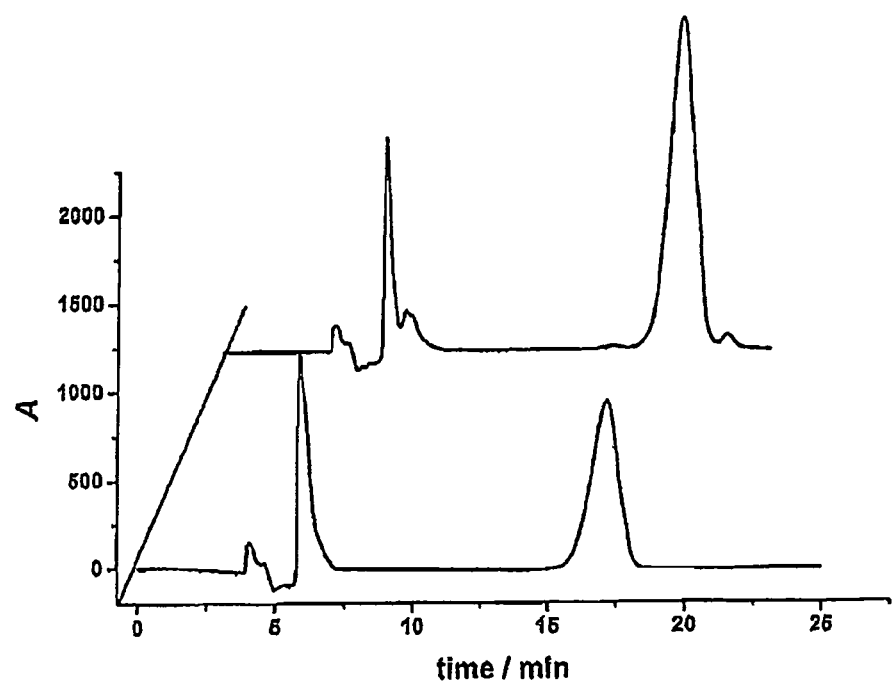

FIG. 4: Chiral HPLC detection of the (R)-mandelic acid. Pure (R)-mandelic acid (10 mM) in methanol (front), mandelic acid extraction from a racemic mandelonitrile conversion with *E. coli* BL21 pAT-NitAf (rear).

Figure 5:
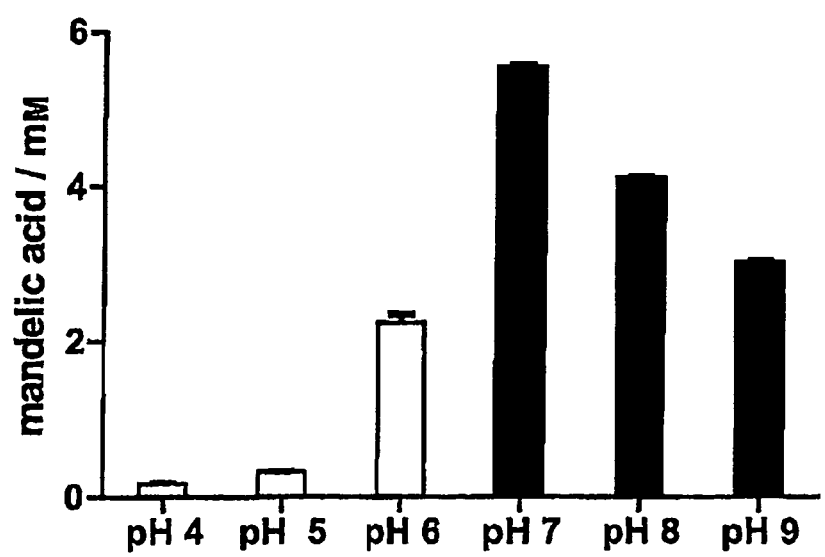

FIG. 5: pH-dependence of the conversion rate of (R,S)-mandelonitrile to R-mandelic acid. The reaction was carried out either in 50 mM acetate buffer (open bars) or 50 mM tris-HCl buffer (filled bars). Reaction time was 48 h at 37° C.

Figure 6:
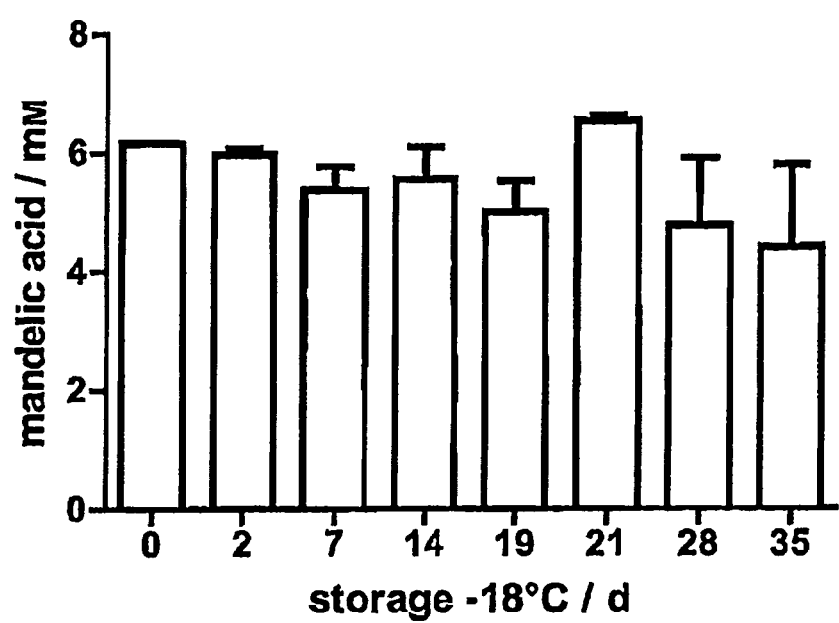

FIG. 6: Stability of the whole cell biocatalyst during storage at −18° C. The cells were frozen in media containing 20% glycerol and after thawing a conversion (mandelic acid production) by *E. coli* BL21 (DE3) pAT-NitAf in 50 mM phosphate buffer pH 7.5, 10 mM mandelonitrile, over 120 h at 37° C. was started.

Figure 7:
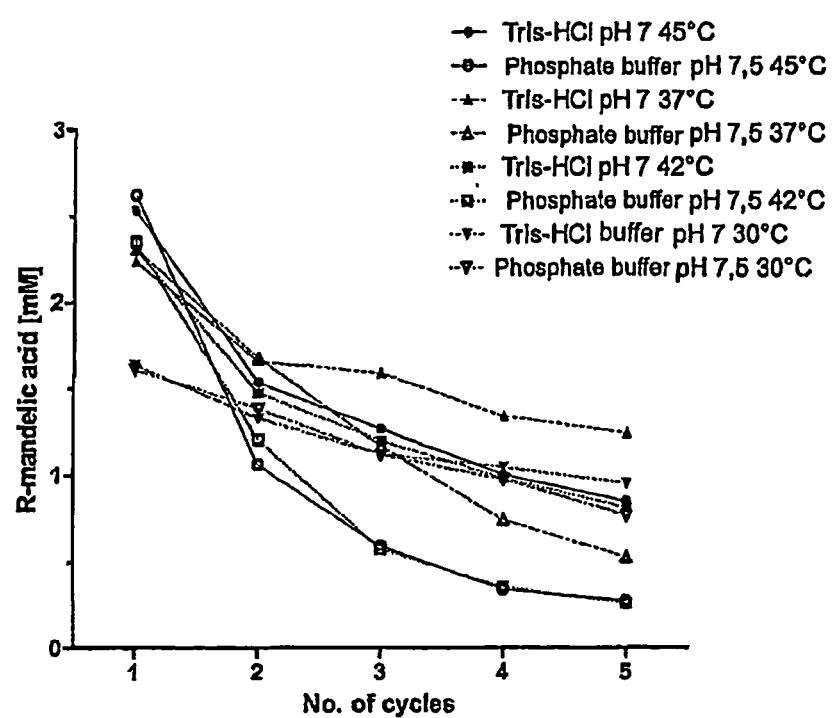

FIG. 7: Reusability of *E. coli* BL21 (DE3) pAT-NitAf at different buffer and temperature conditions. Each cycle corresponds to a conversion period of 24 h. Subsequently, the biocatalyst was removed by centrifugation (60 s at 13000 rpm), resuspended in fresh buffer, combined with fresh substrate (final concentration 10 mM) and incubated for a further 24 h. Filled symbols represent Tris-HCl buffer (50 mM, pH 7), open symbols represent sodium phosphate buffer (50 mM, pH 7.5). 45° C. (●/○), 42° C. (□/■), 37° C. (▲/△), 30° C. (▼/▽).

Figure 8:
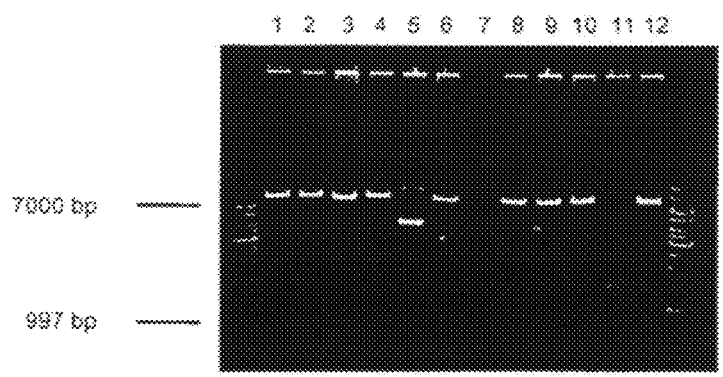

FIG. 8: Restriction digestion of plasmid DNA using KpnI and XhoI. Lane 1) 1 kb Marker, 2)-12) Plasmid DNA from transformants, digested using KpnI/XhoI 13) 1 kb Marker.

Figure 9:
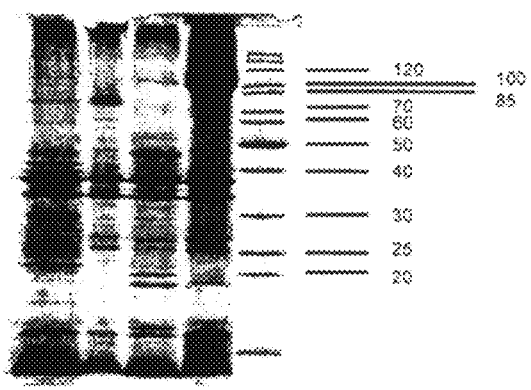

FIG. 9: Isolated outer membrane following trypsin digestion of clones *E. coli* UT 5600 (DE3) pAT-NitAf and pAT-NitSc. Lane 1) pAT-NitSc, trypsin-digested 2) pAT-NitSc, non-digested 3) pAT-NitAf, Proteinase K-digested 4) pAT-NitAf, non-digested 5) Molecular Weight Standard (kDa).

Figure 10:
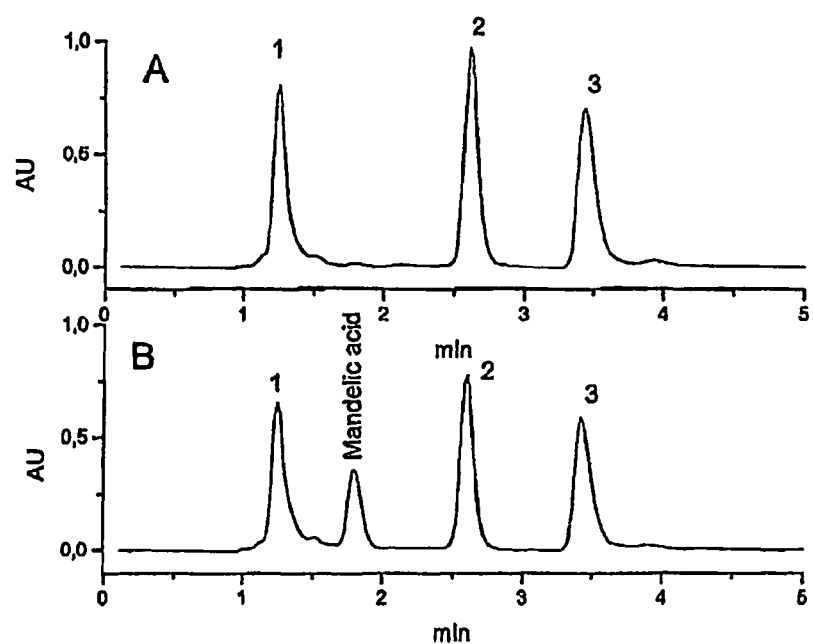

FIG. 10: HPLC analysis following conversion of mandelonitrile by *E. coli* BL21 (DE3) pAT-NitAf.
A) Negative control. *E. coli* BL21 (DE3), $OD_{578}=10$, incubation time: 120 h/30° C.

1) Solvent front of HPLC, 2) Mandelonitrile, 3) Benzaldehyde

B) Conversion by *E. coli* BL21 (DE3) pAT-NitAf, $OD_{578}$=10, incubation time: 120 h/30° C. 1) Solvent front of HPLC, 2) Mandelonitrile, 3) Benzaldehyde.

Figure 11:
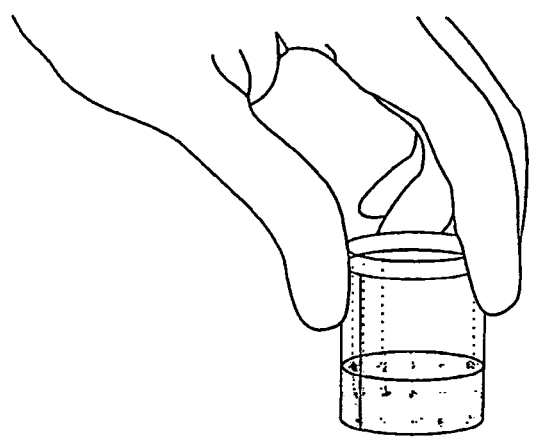

FIG. 11: Mandelic acid produced using the recombinant whole cell biocatalyst *E. coli* BL21 (DE3) pAT-NitAf.

Figure 12:
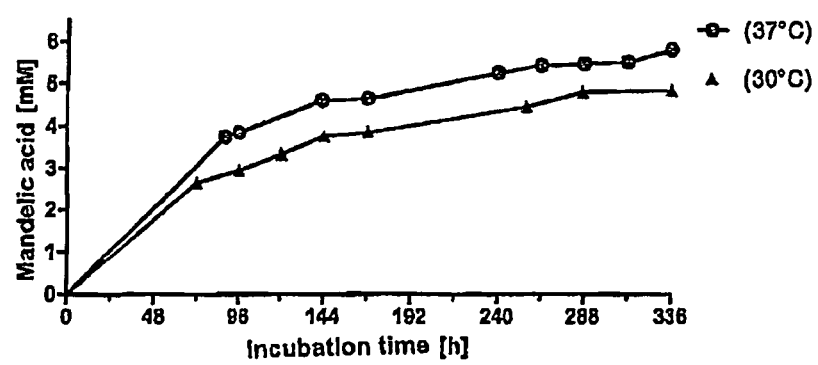

FIG. 12: Mandelic acid production by *E. coli* BL21 (DE3) pAT-NitAf at 30° C. and 37° C., respectively, in phosphate buffer, pH 7.5. At $OD_{578}$=1 cells were induced using 1 mM IPTG for 1 h at 30° C. The substrate concentration at time t=0 was 10 mM mandelonitrile.

Figure 13:
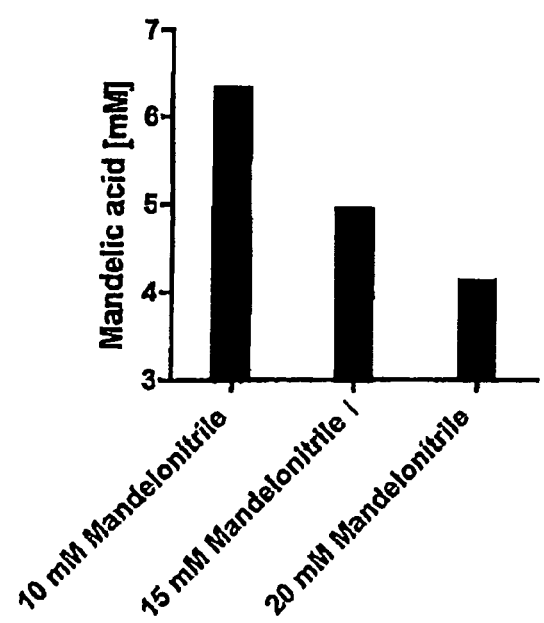

FIG. 13: Mandelic acid production by *E. coli* BL21 (DE3) pAT-NitAf at 37° C. in phosphate buffer, pH 7.5 and using various substrate concentrations. At $OD_{578}$=1 cells were induced using 1 mM IPTG at $OD_{578}$=1 for 1 h at 30° C. Conversion then took place for 120 h.

Figure 14:
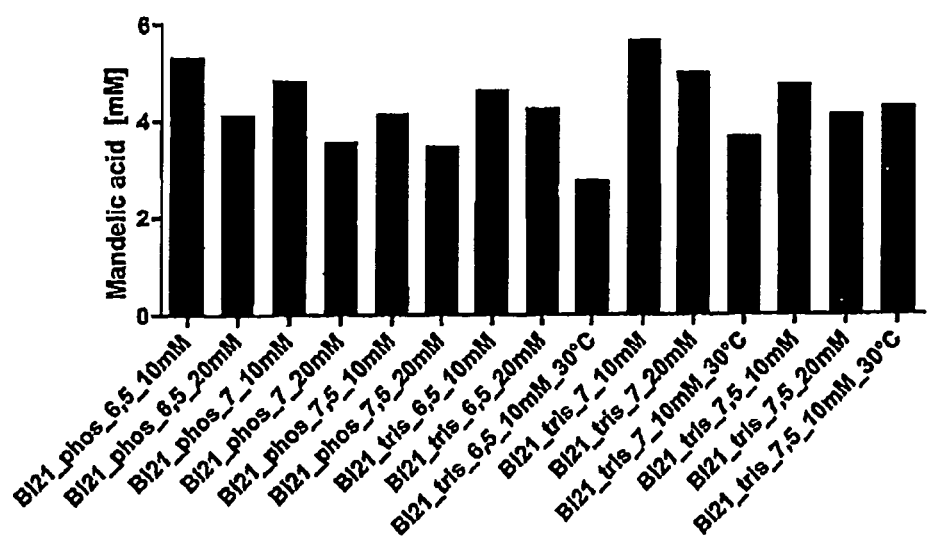

FIG. 14: Mandelic acid production by *E. coli* BL21 (DE3) pAT-NitAf at 37° C. (exceptions as indicated in the Figure) in various buffer systems. At $OD_{578}$=1 cells were induced using 1 mM IPTG for 1 h at 30° C. The substrate concentration at time t=0 was 10 mM mandelonitrile and conversion took place for 120 h.

Figure 15:
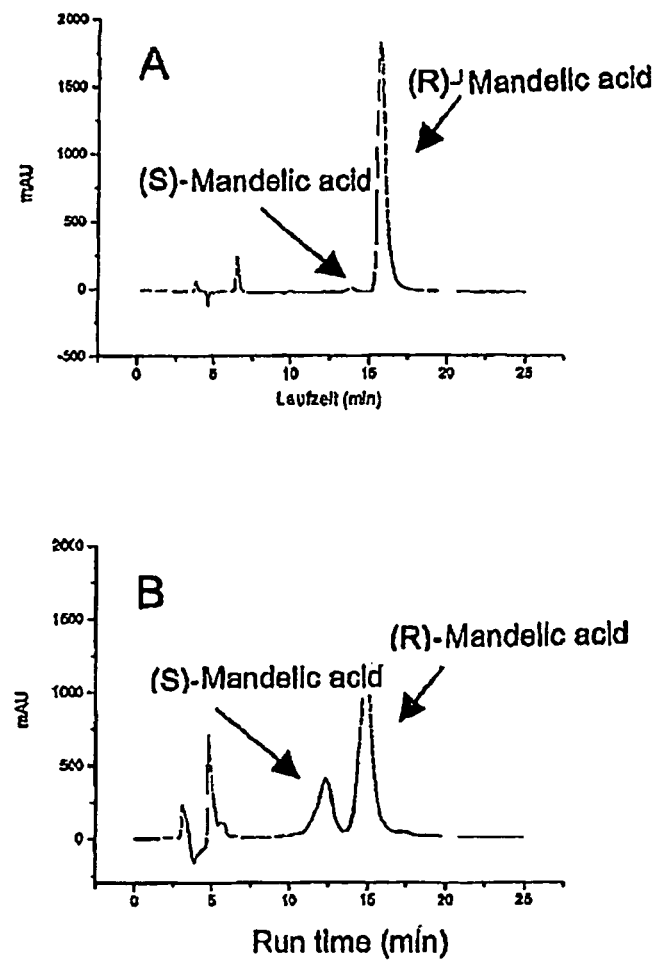

FIG. 15: Detection of the production and identity of (R)-mandelic acid by *E. coli* BL21 (DE3) pAT-NitAf over a period of 5 d. Chiral-OM column (company CS-Chromatographie Service) with hexane:2-propanol:TFA (90:10:0.1), Flow: 0.5 ml/min. Detection at 210 nm. A) Analysis of cell supernatant of *E. coli* BL21 (DE3) pAT-NitAf, extracted with ethyl acetate. B) Racemic mandelic acid combined with the conversion from A).

Figure 16:
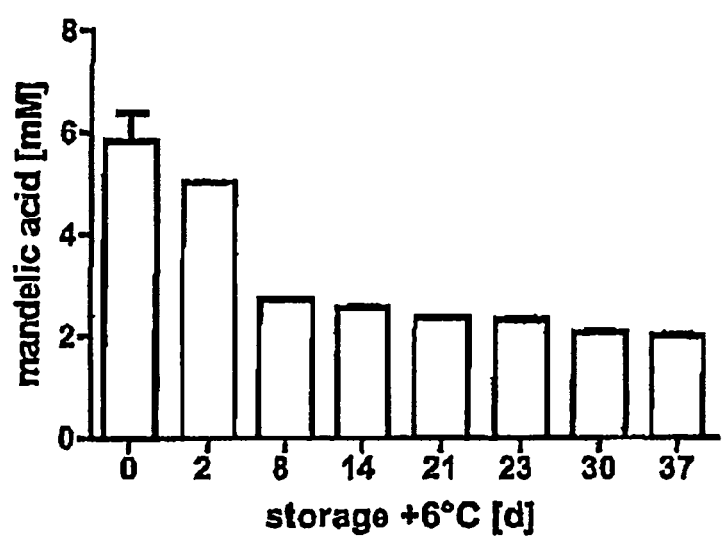

FIG. 16: Mandelic acid production after different storage times at 6° C. (FIG. 16). Conversion by *E. coli* BL21 (DE3) pAT-NitAf in 50 mM phosphate buffer pH 7.5, 10 mM mandelonitrile, 120 h at 37° C.

Figure 17:
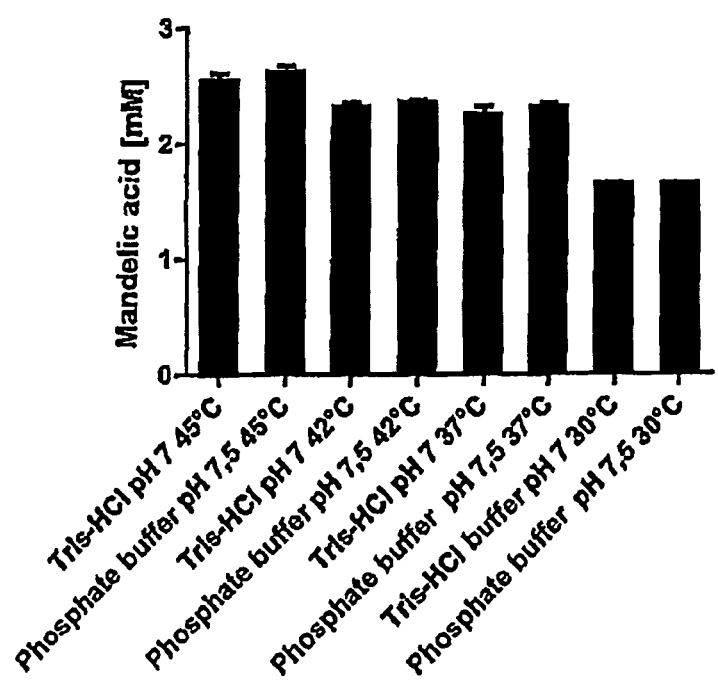

FIG. 17: Mandelic acid production by *E. coli* BL21 (DE3) pAT-NitAf in different buffers and at different temperatures for 24 h each, with 10 mM mandelonitrile at 1000 rpm in a Thermomixer.

Figure 18:
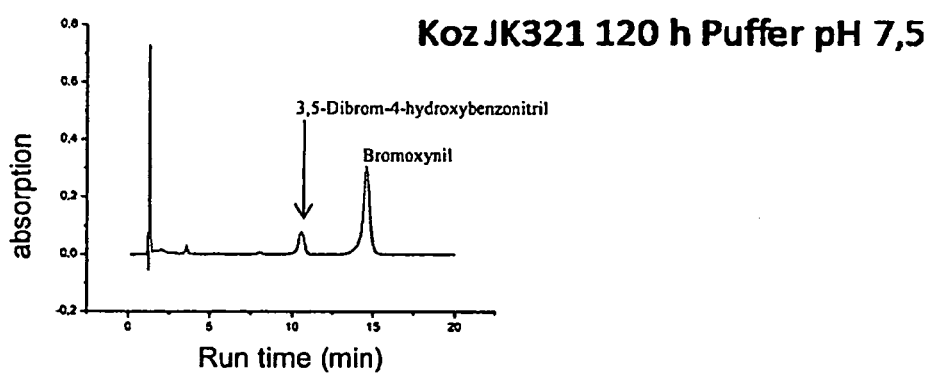

FIG. 18: Detection of the production of 3,5-dibromo-4-hydroxy-benzoic acid by *E. coli* JK321 pAT-NitKp. Incubation time 120 h, $OD_{578}$=10, Substrate 2.5 mM bromoxynile.

EXAMPLES

The following examples demonstrate that the present inventors have been able to identify three nitrilase genes from different organisms and to clone said genes into the autodisplay system.

Example 1

Nitrilase from *Alcaligenes faecalis*

Whole cell biocatalysts are attractive technological tools for the production of bulk and rare chemicals, especially when regio- or enantioselective synthesis is required. In the present study, a whole cell biocatalyst for the synthesis of (R)-mandelic acid using mandelonitrile as substrate was constructed. For this purpose the nitrilase from *Alcaligenes faecalis* subsp. *faecalis* ATCC 8750 was expressed on the surface of *Escherichia coli* (*E. coli*) using autodisplay. The autodisplay system is a powerful surface display system for Gram-negative bacteria and is based on the autotransporter pathway. With this technology it was possible to express the multihomomeric nitrilase in an active form on the surface of *E. coli* and to produce enantiomerically pure (R)-mandelic acid with an enantiomeric excess >99%. The integration of the nitrilase-autotransporter fusion protein in the outer membrane was monitored by SDS-PAGE and the surface exposure of the enzyme could be verified by a protease accessibility test. Under optimized conditions it was possible to produce 2.6 mm of (R)-mandelic acid within 24 h with a bacteria suspension of $OD_{578}$ 10 in a small scale biotransformation (1 ml).

As a model for a multihomomeric enzyme the nitrilase from *Alcaligenes faecalis* subsp. *faecalis* ATCC 8750 was used.

The nitrilase was accessible for protease cleavage during whole cell digestion and showed the same substrate inhibition for benzaldehyde as did the free enzyme.

Results
Fusion Protein Construction

The nitrilase gene was amplified by polymerase chain reaction (PCR) from genomic DNA of *Alcaligenes faecalis* subsp. *faecalis* ATCC 8750 by using oligonucleotides deduced from published sequence data (see Experimental section). The PCR primers added an XhoI site at the 5' and a KpnI site at the 3' end of the nitrilase encoding region, which were required for the fusion of the nitrilase in frame to the autotransporter domains needed for autodisplay. As vector backbone, encoding the autotransporter framework, pET-Adx was employed as described previously (Jose, 2001). The resulting PCR product was ligated into XhoI/KpnI cleaved pET-Adx, replacing the former Adx passenger to give pAT-NitAf. The resulting autotransporter fusion protein exhibits a typical structure, containing a signal peptide, the nitrilase as passenger, a transmembrane linker and the β-barrel (FIG. 1). The signal peptide derived from the cholera toxin β subunit (CTB) is used for the transport through the inner membrane. The β-barrel (transporter domain of an autotransporter) for the translocation of the passenger through the outer membrane, and the linking region (transmembrane linker) for achieving full surface access, were originated from AIDA-I (Jose, 2001).

The resulting mature fusion protein encoded by pAT-NitAf has a predicted molecular mass of around 90 kDa after processing by the signal peptidase. pAT-NitAf was transformed into *E. coli* BL21 (DE3), an OmpT negative mutant, preventing cleavage of the displayed nitrilase. This strain was termed *E. coli* BL21 (DE3) pAT-NitAf.

Expression of the Nitrilase Autotransporter Fusion Protein

The protein biosynthesis of the artificial fusion protein was started by addition of 1 mM IPTG according to the experimental section. To investigate, whether the nitrilase is fully exposed to the surface or to the periplasm, a whole cell digestion with intact cells of *E. coli* BL21 (DE3) pAT-NitAf was performed. Because the outer membrane of *E. coli* is not permeable for proteases like proteinase K or trypsin, degradation of a protein by externally added protease must be due to its surface exposure. The expression and whole cell digestion was monitored by sodium dodecylsulfate polyacrylamide gel electrophoresis (SDS-PAGE). Subsequent staining with Coomassie brilliant blue showed that addition of proteinase K led to a great reduction of the fusion protein band (FIG. 2).

A sensitive marker for the integrity of the analyzed cells is the intensity of the protein bands of Omp F/C and OmpA. There should be no change in the ratio of the two Omp bands in the digested and the undigested sample. If the band of OmpA disappears, the outer membrane got leaky and the periplasmic moiety of OmpA was degraded by proteinase K. In our experiments, the size and the amount of OmpA was identical in protease treated and not treated cells.

In summary we conclude that almost all passenger enzymes were exposed to the bacterial surface.

Enzyme Activity of Surface Displayed Nitrilase

For assaying *E. coli* BL21 (DE3) cells harboring the pAT-NitAf plasmid were adjusted to an optical density at 578 nm ($OD_{578}$) of 10 in 50 mM sodium phosphate buffer pH 7.5 in a total volume of 1 ml. Because the enzyme is described to show a substrate-specificity for hydroxynitriles, racemic mandelonitrile was used as substrate at a final concentration of 10 mM. The bioconversion was analyzed by HPLC and produced mandelic acid was calculated. The first bioconversions were undertaken with cells induced with IPTG at $OD_{578}$ 0.5. This led to a production of 2.1 mM mandelic acid after a bioconversion of 72 h. Further incubation up to 120 h did not result in a further increase of produced mandelic acid. The bioconversion could be significantly improved in the magnitude of two by induction with IPTG at $OD_{578}$ of 1. With this modification the bioconversion did not level off at 72 h, but in contrary increased during the observation period of 120 h to a total of 6.6 mM mandelic acid (FIG. 3). The amount of added substrate was limited due to the occurrence of enzyme inhibition caused by free benzaldehyde, which is formed spontaneously by degradation of mandelonitrile (Yamamoto et al., 1992).

Conversion of Mandelonitrile to Mandelic Acid

A HPLC method has been developed to separate the substrate (mandelonitrile) from the product (mandelic acid) and to detect same. Using *E. coli* BL21 (DE3) pAT-NitAf conversion of mandelonitrile to mandelic acid was confirmed (FIG. 10). HPLC analysis also revealed that in an aqueous system mandelonitrile is present in equilibrium with benzaldehyde (+HCN) as expected (FIG. 10). Adaptation of several reaction parameters resulted in a product concentration of 2.4 mM, which corresponds to a masse of 0.36 mg per 1 ml sample, after 120 h starting from a substrate concentration of 5 mM when a cell suspension of $OD_{578}$ of 10 was used (FIG. 11).

Enantiomeric Excess

The next step was to verify the enantiomeric excess of the produced mandelic acid. For this purpose mandelic acid was extracted from the aqueous buffer by solvent extraction with ethylacetate. The extracted mandelic acid was solved in methanol and directly used for chiral HPLC analysis. The enantiomeric excess (ee) was determined to be ee>99% for the bioconversion at 37° C. (FIGS. 4 and 15A). This shows that the surface displayed nitrilase of *A. faecalis* is capable to produce (R)-mandelic acid with high enantiomeric purity. From FIG. 15A it is evident that almost exclusively a peak characteristic of the retention time of the (R)-enantiomer of mandelic acid was detectable. The calculated enantiomeric purity was more than 99%. FIG. 15B shows the identity of (R)-mandelic acid as determined by spiking of pure (R)- and (S)-enantiomers with the conversion from FIG. 15A.

pH Optimum

Although the pH optimum of the *Alcaligenes faecalis* nitrilase was published previously to be pH 7.5 we investigated if there was a shift in the pH optimum due to the surface exposure. The cells were resuspended in acetate buffer or in Tris-HCl buffer (both 50 mM) to a final $OD_{578}$ of 10. After 120 h of incubation at 37° C. the supernatant was analyzed by HPLC and the converted amount of mandelic acid was calculated. We determined the pH optimum at pH 7 with a conversion of 5.5 mM mandelic acid. A strong loss of activity between pH 7 and pH 8 was detectable. The additional investigated phosphate buffer pH 7.5 led to a conversion of only 4.4 mM mandelic acid under otherwise same conditions (data not shown) (FIG. 5).

With the optimization of reaction temperature and pH value it was possible to convert up to 2.6 mM mandelic acid within 24 h. Mandelamide was not detectable at any time.

Kinetics

In a series of experiments several parameters have been analyzed for their influence on mandelic acid production on a laboratory scale. FIG. 12 represents the kinetics of mandelic acid production at different temperatures. At 37° C. a product concentration increased by about 20% was detected as compared to a conversion at 30° C. The progression of the conversion at both, 30° C. and 37° C., also demonstrated that the concentration of the mandelic acid produced increases only slowly after a conversion of about 144 h.

Substrate Concentration

Further, the influence of substrate concentration on the production of mandelic acid was analysed. In an aqueous solution the substrate mandelonitrile is in equilibrium with benzaldehyde and HCN. However, at excessive concentrations benzaldehyde exhibits a toxic effect on the cells, thus limiting an increase of substrate concentration as shown in FIG. 13. A further reduction of nitrile concentration to below 10 mM did not result in a further increase of the production rate suggesting the use of 10 mM mandelonitrile as the optimal substrate concentration.

Different Buffer Systems

Comparative examinations of mandelic acid production using the whole cell catalyst *E. coli* BL21 (DE3) pAT-NitAf have also been performed using different buffer systems. FIG. 14 shows that best results were achieved using a Tris-buffered solution of pH 6.5 as compared to any other buffer used.

Storage Stability

To determine the storage stability of the constructed whole cell biocatalyst, IPTG-induced cells of *E. coli* BL21 (DE3) pAT-NitAf were adjusted to an OD578 of 50 in 50 mM sodium phosphate buffer pH 7.5, containing 20% (v v-1) glycerol and stored at −18° C. Glycerol was added to the samples at −18° C. as an antifreeze agent in oder to prevent lysis of the cells. At different time intervals samples were washed once in phosphate buffer and adjusted to an OD578 of 10. Alternatively, following IPTG induction aliquots of cells were stored at 6° C. in the fridge and were subjected to a nitrilase assay after different storage times. Reaction was started by addition of 10 mM mandelonitrile and the samples were incubated for 120 h at 37° C. After storage of 35 days at −18° C. the cells still retained 72% of their initial activity (FIG. 6). After one week the activity of the whole cell catalyst at +6° C. was only about 50% of the initial activity (FIG. 16). Also in these experiments this correlated with the observed lysis of cells. Here, again, it is apparent that a proportion of the cells exhibits a relatively stable residual activity over the measured period of time.

Temperature Dependence of the Whole Cell Catalyst

It is described that the optimum temperature of the enzyme purified from *A. faecalis* is 40-45° C. These findings are confirmed by FIG. 17 describing tests of temperature in the range from 30° C. to 45° C. The use of phosphate buffer or Tris buffer in the reaction mixture does not appear to have a particular influence.

Reusability of the Whole Cell Catalyst (FIG. 7)

To investigate the reusability and stability of the whole cell biocatalyst 5 cycles of 24 h conversion reactions were performed at different buffer and temperature conditions. A "cycle" is a 24 h conversion reaction followed by centrifugation of the *E. coli* cells and addition of fresh substrate for the next cycle. The highest yield within 24 h was reached with *E. coli* BL21 (DE3) pAT-NitAf in sodium phosphate buffer (pH 7.5, 45° C.) with 2.62 mM mandelic acid, but the activity dropped fast to a minimum of only 10% of the original activity after 5 cycles. With Tris-HCl buffer (pH 7, 45° C.) a conversion of 2.53 mM mandelic acid was achievable within 24 h, after 5 cycles more than 33% of the primary conversion rate could be obtained. The activity of the cells in Tris-HCl (37° C.) dropped from 2.24 mM in the first cycle to 1.25 mM after 5 cycles, this represents more than 55% residual activity. During the first cycle there were only minor differences in the production rate between cells resuspended in sodium phosphate buffer or in Tris-HCl buffer, but in contrast the overall performance was always better in the test samples with Tris-HCl buffer.

Experimental Section

Bacterial Strains and Plasmids

For subcloning purposes E. coli TOP10 [F⁻ mcrA Δ(mrr-hsd RMS-mcrBC) φ80lacZΔM15 ΔlacX74 recA1 araD139 Δ(ara-leu) 7697 galU galK rpsL (Str$^R$) endA1 nupG] from Invitrogen (Carlsbad, Calif., USA) was used. *Escherichia coli* BL21 (DE3) [B, F⁻, dcm, ompT, Ion, hsdS (rB⁻ mB⁻), gal, λ (DE3)] was used for the expression of autotransporter fusion proteins.

E. coli strains were routinely grown at 37° C. in Luria-Bertani (LB) medium containing ampicillin (100 μgmL⁻¹) with vigorous shaking (200 rpm). Solid media were prepared by the addition of agar (1.5%, wv⁻¹) to the media.

The plasmid pCR®4-TOPO® from Invitrogen (Carlsbad, Calif., USA) was used for subcloning the nitrilase gene. The construction of plasmid pET-Adx04 encoding the AIDA-I autotransporter framework was described previously (Rustler et al., 2008; U.S. Pat. No. 6,180,359). FIG. 8 shows plasmids isolated from 11 transformants, wherein the correct DNA fragment of about 1 kb corresponding to the PCR fragment was detected within the correct autotransporter plasmid (about 7 kb) in 7 clones following digestion using KpnI and XhoI.

Recombinant DNA Techniques

The gene enconding the nitrilase was amplified from genomic DNA of *Alcaligenes faecalis* subsp. *faecalis* ATCC 8750 (LGC Standards GmbH, Wesel, Germany).

The primers for the amplification of the nitrilase gene were derived from already described sequence information for the nitrilase gene of *A. faecalis* ATCC 8750 (Kaul et al., 2007). The forward primer Nit-XhoI (5'-CCG CTCGAGCAGACAAGAAAAATCGTCC) and the reverse primer Nit-KpnI (3'-GG GGTACCGGACGGTTCTTGCACC) were used to amplify a 1073 by fragment containing the nitrilase gene. To facilitate cloning of the PCR product, XhoI and KpnI restriction sites were added (underlined parts in the primer sequences represent the restriction site for the respective enzyme). The PCR reaction contained 10 ng of genomic DNA, appropriate amount of Eppendorf PCR Mastermix from Eppendorf (Hamburg, Germany), 1 μL (10 μM stock solution) of the forward and reverse primer (Sigma-Aldrich Chemical Company, Milwaukee, USA) in a volume of 10 μL. The PCR reaction was performed in an Eppendorf Mastercycler gradient from Eppendorf (Hamburg, Germany). The PCR protocol consisted of an initial denaturation step of 5 min at 95° C., followed by 30 cycles of 30 s at 94° C., 1 min at 64° C., 1 min at 72° C. and ending with a final elongation step of 6 min at 72° C.

The PCR product was directly used for subcloning into the pCR®4-TOPO® Vector according to the manufacturer's instructions. Preparation of plasmid DNA was performed as described elsewhere. The resulting plasmid was digested with XhoI/KpnI and purified by agarose gel electrophoresis using the Qiagen Gel Extraction Kit (Qiagen, Hilden, Germany).

The resulting fragment was inserted into XhoI/KpnI cleaved pET-Adx04 vector, where it replaced the gene coding for Adx04, to give pAT-NitAf.

Outer Membrane Preparation and SDS-PAGE

E. coli cells were grown overnight and an appropriate amount of the culture was used for inoculation of LB medium containing 2-mercaptoethanol (10 mM) and ampicillin (100 μgmL⁻¹). Cells were cultured at 37° C. (200 rpm) until an optical density (OD$_{578}$) of 0.5 or 1 was reached. For inducible expression IPTG (1 mM final concentration) purchased from Roth (Karlsruhe, Germany) was added. After 60 min at 30° C. the cells were harvested and washed with Tris-HCl (0.2 M, pH 8.2). For the protease accessibility test the cells were resuspended in 2 ml Tris-HCl (0.2 M, pH 6.8) containing 25 μL of a proteinaseK-solution (2%) and incubated for 60 min in a water bath at 37° C. Differential cell fractionation was performed according to a modification of the method of Hantke (Hantke, 1981).

For SDS-PAGE outer membrane isolates were diluted 1:2 with sample buffer which consisted of Tris-HCl (100 mM, pH 6.8), sodium dodecyl sulfate (4%), bromophenol blue (0.2%), 2-mercaptoethanol (2%), dithiothreitol (0.2 M) and glycerol (20%), boiled for 5 min and analyzed on 10% polyacrylamide gels. Proteins were stained with Coomassie brilliant blue and Pageruler unstained protein ladder purchased from Fermentas (St. Leon-Rot, Germany) was used for size determination.

Performing a Standard Conversion

A standard experiment is carried out as follows: A pre-culture of recombinant *E. coli* BL21 (DE3) pAT-NitAf strain is used to inoculate a main culture in a ratio of 1:100 and cultivated at 37° C. and 200 rpm in a shaking incubator. Upon reaching an OD$_{578}$ of 1 IPTG is added for induction using a final concentration of 1 mM. Induction then takes place for one hour at 30° C. and 200 rpm. After that cells are washed once with 50 mM phosphate buffer, pH 7.5 and finally adjusted to an OD$_{578}$ of 10 using the same buffer. 1 ml aliquots of said cell suspension are then combined with 20 μl mandelonitrile (0.5 M) and incubated at different temperatures (in particular 37° C.) in a thermomixer at 1000 rpm or 200 rpm. Samples were taken at different time intervals, centrifuged (6000×g, 5 min) and sterile filtered with a 0.2 μm polyethersulfone membrane filter purchased from VWR (Darmstadt, Germany). The supernatant was directly analyzed by HPLC. No further bioconversion was detectable after sterile filtration.

Analytical Methods

Nitrile conversion was analysed by HPLC (Millenium Chromatography Manager 3.2), equipped with a diode array detector 996 and 2695 separation module from Waters (MA, USA). For the achiral analysis, a reversed phase column [100 mm×4.6 mm (internal diameter), filled with Hypersil ODS 5 μm diameter particles] from Hewlett Packard (Böblingen, Germany) was used to identify the conversion products which were detected spectrophotometrically at 210 nm. Methanol (40% vv⁻¹) and phosphoric acid (0.1%) in water was used as mobile phase for the HPLC separation. For separation of the mandelic acid enantiomers a chiral phase column [150 mm×4.6 mm (internal diameter), filled with Reprosil Chiral-OM 5 μm diameter particles] from CS-Chromatographie Service (Langerwehe, Germany) was used.

The mobile phase consisted of hexane (90% vv⁻¹), isopropyl alcohol (10% vv⁻¹) and trifluoroacetic acid (0.1% vv⁻¹). The mandelic acid was extracted from the bioconversion samples as described elsewhere, with the slight modification that ethyl acetate was used instead of dichlormethane (Yamamoto, 1991).

Example 2

Nitrilase from *Klebsiella pneumoniae*

The nitrilase gene from *K. pneumoniae* was amplified using PCR and inserted into a corresponding autodisplay vector following intermediate cloning into an *E. coli* standard vector and sequence analysis, as described in Example 1. The autodisplay construct encoding a fusion protein comprising *K. pneumoniae* nitrilase, an autotransporter domain, a transmembrane linker, and a signal peptide, as described for pAT-NitAf in Example 1, is termed pAT-NitKp. The corresponding *E. coli* strain displaying the fusion polypeptide on the surface is termed *E. coli* BL21 (DE3) pAT-NitKp.

Detection of expression and surface localization of the *Klebsiella pneumoniae* nitrilase was carried out analogous to *Alcaligenes faecalis* nitrilase (cf. Example 1).

It is well-known from literature that said nitrilase exhibits a very high substrate specificity for bromoxynile. Said toxic compound is widely used as a herbicide in agriculture and is applied in industrial scale in Germany each year. The corresponding carboxylic acid exhibits lower toxicity and stability in nature.

Production of 3,5-dibromo-4-hydroxy-benzoic acid from bromoxynile by *E. coli* JK321 pAT-NitKp is shown in FIG. 18. This Figure indicates that the *K. pneumoniae* nitrilase expressed on the surface of an *E. coli* cell is capable of converting a nitrile into its corresponding carboxylic acid.

Example 3

Nitrilase from *Saccharomyces cerevisiae*

The nitrilase gene of *S. cerevisiae* was amplified by PCR and cloned, as described in Example 1. Sequence analysis revealed 100% identity to the *S. cerevisiae* nitrilase sequence obtained from databases. The nitrilase was cloned into *E. coli* as a fusion protein comprising an autotransporter domain, a transmembrane linker, and a signal peptide, as described in Example 1. Again, sequence analysis revealed 100% identity to the sequence from databases. Detection of expression was carried out analogous to Example 1.

The autodisplay construct encoding a fusion protein comprising *S. cerevisiae* nitrilase, an autotransporter domain, a transmembrane linker, and a signal peptide, as described for pAT-NitAf in Example 1, is termed pAT-NitSc. The corresponding *E. coli* strain displaying the fusion polypeptide on the surface is termed *E. coli* BL21 (DE3) pAT-NitSc.

It was found that following IPTG induction the fusion protein comprising the *S. cerevisiae* nitrilase was localized on the surface. Trypsin digestion of whole cells es described in Example 1 was applied. The results are summarized in FIG. 9.

References

1. Jose J, Meyer T F (2007) The autodisplay story, from discovery to biotechnical and biomedical applications. Microbiol. Mol Biol Rev 71 (4): 600-19
2. Nagasawa T, Mauger J, Yamada H (1990) A novel nitrilase, arylacetonitrilase, of *Alcaligenes faecalis* JM3, Purification and characterization. Eur J Biochem 194(3): 765-72
3. Yamamoto K, Oishi K. Fujimatsu I, Komatsu K (1991) Production of R-(–)-mandelic acid from mandelonitrile by *Alcaligenes faecalis* ATCC 8750. Appl Environ Microbiol. 57(10): 3028-32
4. Rey P, Rossi J C, Taillades J, Gros G, Nore O (2004) Hydrolysis of nitriles using an immobilized nitrilase: applications to the synthesis of methionine hydroxy analogue derivatives. J Agric Food Chem 52 (26): 8155-62
5. Kiziak C, Conradt D, Stolz A, Mattes R, Klein J (2005) Nitrilase from *Pseudomonas fluorescens* EBC191: cloning and heterologous expression of the gene and biochemical characterization of the recombinant enzyme. Microbiology 151 (Pt 11): 3639-48.
6. Kaul P, Stolz A, Banerjee UC (2007) Cross-Linked Amorphous Nitrilase Aggregates for Enantioselective Nitrile Hydrolysis. Adv Synth Catal 349: 2167-2176
7. Banerjee A, Dubey S, Kaul P, Barse B, Piotrowski M, Banerjee UC (2008) Enantioselective Nitrilase from *Pseudomonas putida*: Cloning, Heterologous Expression, and Bioreactor Studies. Mol Biotechnol [Epub ahead of print]
8. Luo H, Fan L, Chang Y, Ma J, Yu H, Shen Z (2008) Gene Cloning, Overexpression, and Characterization of the Nilrilase from *Rhodococcus rhodochrous* tg1-A6 in *E. coli*. Appl Biochem Biotechnol [Epub ahead of print]
9. Rustler S, Motejadded H, Altenbuchner J, Stolz A (2008) Simultaneous expression of an arylacetonitrilase from *Pseudomonas fluorescens* and a (S)-oxynitrilase from *Manihot esculenta* in *Pichia pastoris* for the synthesis of (S)-mandelic acid. Appl Microbiol Biotechnol 80 (1): 87-97
10. Industrial scale process for the preparation of 2-hydroxy-4-methylbutyric acid using a nitrilase. U.S. Pat. No. 6,180,359
11. Ress-Löschke M. Friedrich T, Hauer B, Mattes R (1998) Verfahren zur Herstellung chiraler Carbonsäuren aus Nitrilen mit Hilfe einer Nitrilase oder Mikroorganismen, die ein Gen für eine Nilrilase enthalten. German Patent Application DE 19848129A1
12. J. Jose, Appl. Microbiol. Biotechnol. 2006, 69, 607-614.
13. J. Jose, R. Bernhardt, F. Hannemann, J. Biotechnol. 2002, 95, 257-268.
14. J. Jose, S. von Schwichow, ChemBioChem 2004, 5, 491-499.
15. K. V. Thimann, S. Mahadevan, Arch. Biochem. Biophys. 1964, 105, 133-141.
16. A. Banerjee, R. Sharma, U. C. Banerjee, Appl. Microbiol. Biotechnol. 2002, 60, 33-44.
17. R. N. Thuku, D. Brady, M. J. Benedik, B. T. Sewell, J. Appl. Microbiol. 2009, 106, 703-727.
18. K. Yamamoto, I. Fujimatsu, K.-I. Komatsu, J. Ferment. Bioeng. 1992, 73, 425-430.
19. J. Jose, R. Bernhardt, F. Hannemann, ChemBioChem 2001, 2, 695-701.
20. J. Maurer, J. Jose, T. F. Meyer, J. Bacteriol. 1997, 179, 794-804.
21. H. C. Birnboim, J. Doly, Nucleic Acids Res. 1979, 7, 1513-1523.
22. K. Hantke, Mol Gen Genet. 1981, 182, 288-292.
23. Henderson I et al., 2004. Type V protein secretion pathway: the autotransporter story. Microbiology and Molecular Biology Reviews, 68(4), 692-744.
24. Niewert U., Frey A., Voss T., Le Bouguen C., Baljer G., Franke S., Schmidt M A. The AIDA Autotransporter System is Associated with F18 and Stx2e in *Escherichia coli* Isolates from Pigs Diagnosed with Edema Disease and Postweaning Diarrhea. Clin. Diagn. Lab. Immunol. 2001 January, 8(1):143-149; 9.
25. Buchholz, Kasche and Bornscheuer (2005). Biocatalysts and Enzyme Technology. Enzymes in Organic Chemistry, Wiley-VCH-Verlag, Weinheim.
26. Hartl, F. U., and Hayer-Hartl, M. (2002) Science 295 (5561):1852-8

The invention claimed is:

1. A method comprising the steps of:
    (i) providing a microorganism comprising a recombinant nitrilase located on its surface, and/or on a membrane preparation of said microorganism,
    (ii) contacting the microorganism and/or the membrane preparation thereof with one or more nitrilase substrates under conditions compatible with nitrilase activity, wherein the nitrilase is fused to a transporter domain of an autotransporter.

2. The method of claim 1, wherein the product of a reaction catalysed by a nitrilase is a carboxylic acid and at least one nitrilase substrate is a nitrile.

3. The method of claim 1, wherein the nitrilase is recombinantly expressed in the microorganism and transported to its surface.

4. The method of claim 1, wherein step (i) comprises
    (a) providing a microorganism comprising a nucleic acid sequence operatively linked with an expression control sequence, said nucleic acid sequence comprising:
        (1) a portion encoding a signal peptide,
        (2) a portion encoding a recombinant nitrilase to be displayed,
        (3) optionally a portion encoding a protease recognition site,
        (4) a portion encoding a transmembrane linker, and
        (5) a portion encoding the transporter domain of an autotransporter,
    (b) culturing the microorganism under conditions, wherein the nucleic acid sequence of (a) is expressed and the expression product of the nucleic acid sequence is displayed on the surface of the microorganism.

5. The method of claim 4, further comprising the step
    (c) producing a membrane preparation from the microorganism of (b)

6. The method of claim 4, wherein the transporter domain of the autotransporter is selected from the group comprising Ssp, Ssp-h1, Ssp-h2, PspA, PspB, Ssa1, SphB1, AspA/NalP, VacA, AIDA-I, IcsA, MisL, TibA, Ag43, ShdA, AutA, Tsh, SepA, EspC, EspP, Pet, Pic, SigA, Sat, Vat, EpeA, EatA, EspI, EaaA, EaaC, Pertactin, BrkA, Tef, Vag8, PmpD, Pmp20, Pmp21, lgA1 protease, App, Hap, rOmpA, rOmpB, ApeE, EstA, Lip-1, McaP, BabA, SabA, AlpA, Aae, NanB, and variants thereof.

7. The method of claim 1, wherein the nitrilase is selected from the group comprising *Alcaligenes* nitrilases, *Klebsiella* nitrilases and *Saccharomyces* nitrilases.

8. The method of claim 1, wherein the microorganism is a Gram-negative bacterium, in particular *Escherichia coli*.

9. The method of claim 1, wherein step (ii) is performed at a pH in the range of about 6.5 to about 7.5.

10. The method of claim 1, wherein step (ii) is performed under aerobic and/or oxidising conditions.

11. The method of claim 2, wherein the nitrile is selected from the group comprising mandelonitrile, prunasin, bromoxynile, ioxynile, chloroxynile, anisonitrile, 3-bromo-4-hydroxybenzonitrile, 3-fluoro-4-hydroxybenzonitrile, 4-hydroxy-3,5-dimethobenzonitrile, benzonitrile, phenylprobionitrile, phenylglycinonitrile, n-butyronitrile, n-valeronitrile, isobutyronitrile and succinonitrile.

12. The method of claim 1, wherein the product of a reaction catalysed by a nitrilase is a carboxylic acid, and said carboxylic acid is produced in an enantiomeric excess of at least about 70%.

13. The method of claim 1, further comprising the step (iii) recovering the microorganism employed in step (ii).

* * * * *

SEQUENCE LISTING

<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: The forward primer Nit-Xhol was used to amplify
    a 1073 bp fragment containing the nitrilase gene of Alcaligenes
    faecalis (Example 1).

<400> SEQUENCE: 1
ccgctcgagc agacaagaaa aatcgtcc                                      28

<210> SEQ ID NO 2
<211> LENGTH: 24
<212> TYPE: DNA
<213> ORGANISM: Artificial Sequence
<220> FEATURE:
<223> OTHER INFORMATION: The reverse primer Nit-Kpnl was used to amplify
    a 1073 bp fragment containing the nitrilase gene of Alcaligenes
    faecalis (Example 1).

<400> SEQUENCE: 2
ggggtaccgg acggttcttg cacc                                          24